United States Patent
Pullar

(10) Patent No.: US 9,555,013 B2
(45) Date of Patent: Jan. 31, 2017

(54) MODULATION OF FIBROBLAST ACTIVITY

(75) Inventor: Christine Elaine Pullar, Leicester (GB)

(73) Assignee: The University of Leicester, Leicester (GB)

( * ) Notice: Subject to any disclaimer, the term of this patent is extended or adjusted under 35 U.S.C. 154(b) by 909 days.

(21) Appl. No.: 12/934,483

(22) PCT Filed: Mar. 27, 2009

(86) PCT No.: PCT/GB2009/000829
§ 371 (c)(1),
(2), (4) Date: Dec. 22, 2010

(87) PCT Pub. No.: WO2009/118541
PCT Pub. Date: Oct. 1, 2009

(65) Prior Publication Data
US 2011/0201691 A1    Aug. 18, 2011

(30) Foreign Application Priority Data

Mar. 27, 2008 (GB) .................................. 0805535.2

(51) Int. Cl.
*A61K 31/137* (2006.01)
*A61K 31/138* (2006.01)

(52) U.S. Cl.
CPC .......... *A61K 31/137* (2013.01); *A61K 31/138* (2013.01)

(58) Field of Classification Search
CPC .............................. A61K 31/138; A61K 31/137
See application file for complete search history.

(56) References Cited

U.S. PATENT DOCUMENTS

| 5,411,737 A | * | 5/1995 | Hsu et al. ..................... 424/411 |
| 5,958,432 A | | 9/1999 | Brenton et al. |
| 2006/0235048 A1 | * | 10/2006 | Weidner ....................... 514/317 |

(Continued)

FOREIGN PATENT DOCUMENTS

| CN | 101244049 | * | 2/2007 | .......... A61K 31/137 |
| DE | 10 2004 045648 A1 | | 3/2006 | |

(Continued)

OTHER PUBLICATIONS

Akutsu et al, British Journal of Pharmacology (2006) 147, 412-421.*

(Continued)

*Primary Examiner* — Savitha Rao
*Assistant Examiner* — Angela Brown-Pettigrew
(74) *Attorney, Agent, or Firm* — K&L Gates LLP

(57) ABSTRACT

The invention includes a method for combating scarring in a subject, the method comprising administering to the subject an agent which positively modulates β2-adrenergic receptor; a method for simultaneously decreasing the amount of TGFβ1 and increasing the amount of TGFβ3 produced by a fibroblast, the method comprising contacting the fibroblast with an agent which positively modulates β2-adrenergic receptor; a method for reducing fibroblast differentiation, the method comprising contacting the fibroblast with an agent which positively modulates β2-adrenergic receptor; and a method of reducing the deposition of collagen in a subject, the method comprising administering to the subject an agent which positively modulates β2-adrenergic receptor.

12 Claims, 16 Drawing Sheets

(56) References Cited

U.S. PATENT DOCUMENTS

2008/0287467 A1* 11/2008 Tamura et al. ............ 514/263.1

FOREIGN PATENT DOCUMENTS

| | | |
|---|---|---|
| EP | 0 769 293 A | 4/1997 |
| EP | 1 719 507 A | 11/2006 |
| WO | WO 01/94319 A | 12/2001 |
| WO | WO 03/097073 A1 | 11/2003 |
| WO | WO 2006/027579 A2 | 3/2006 |
| WO | WO 2006/108176 | 10/2006 |
| WO | WO 2007/137204 A | 11/2007 |
| WO | WO 2008/078096 | 7/2008 |

OTHER PUBLICATIONS

O'Kane et al, Int. J. Biochem. Cell Biol. (1997) 29, 63-78.*
CN 101244049, translation.*
Arora et al., "Compliance of Collagen Gels Regulates Transforming Growth Factor-β Induction of α-Smooth Muscle Actin in Fibroblasts," American Journal of Pathology, vol. 154, No. 3, Mar. 1999, pp. 871-882.
Beausang et al., "A New Quantitative Scale for Clinical Scare Assessment," Plastic & Reconstructive Surgery, vol. 102(6), Nov. 1998, pp. 1954-1961.
Bilski et al., "The Pharmacology of a $β_2$-Selective Adrenoceptor Antagonist (ICI 118,551)," Journal of Cardiovascular Pharmacology (1983), pp. 430-437.
Ghahary et al., "Cell Proliferating Effect of Latent Transforming Growth Factor-β1 is Cell Membrane Dependent," Wound Healing Society (2002), pp. 328-335.
Grinnell, "Fibroblast Biology in Three-Dimensional Collagen Matrices," Trends in Cell Biology, vol. 13, No. 5, May 2003, pp. 264-269.
Ha et al., "Effect of Human Hepatocyte Growth Factor on Promoting Wound Healing and Preventing Scar Formation by Adenovirus-Mediated Gene Transfer," Chinese Medical Journal (2003), vol. 116(7), pp. 1029-1033.
Huang et al., "Synthetic TGF-β Antagonist Accelerates Wound Healing and Reduces Scarring," FASEB J., Jun. 21, 2002, pp. 1269-1270.
Jain et al., "Bosentan for the Treatment of Systemic Sclerosis-Associated Pulmonary Arterial Hypertension, Pulmonary Fibrosis and Digital Ulcers," Expert Opinion Pharmacother., vol. 7(11), pp. 1487-1501.
Johnson, "Molecular Mechanisms of $β_2$-Adrenergic Receptor Function, Response, and Regulation," J Allergy Clin. Immunol., Jan. 2006, vol. 117, pp. 18-24.
Kobilka et al., "cDNA for the Human $β_2$-Adrenergic Receptor," Proc. Natl. Acad. Sci. USA, vol. 84, Jan. 1987, pp. 46-50.
Antoniu, "Pirfenidone for the Treatment of Idiopathic Pulmonary Fibrosis," (2006) Expert Opin. Investig. Drugs, vol. 15(7), pp. 823-828.
Bouros et al., "Interferon-$γ_{1b}$ for the Treatment of Idiopathic Pulmonary Fibrosis," (2006) Expert Opin. Biol. Ther. 6(10), pp. 1051-1060.
Meier et al., "Emerging New Drugs for Scar Reduction," (2006) Expert Opinion in Emerging Drugs, vol. 11(1), pp. 39-47.
Sueblinvong et al., "Novel Therapies for the Treatment of Cystic Fibrosis: New Developments in Gene and Stem Cell Therapy," (2007) Clin. Chest Med., vol. 28(2), pp. 361-379.
Eggleston et al. (1991) Chest 99, 1088-1092 (Abstract only).
BIOSIS Accession No PREV19923140862 and Skipskii et al (1991) Terapevticheskii Arkhiv, vol. 93, 125-127 (Abstract only).
Bargon et al. (1997) European Respiratory Journal, vol. 19, pp. 2307-2311 (Abstract only).
Akutsu et al., "Transforming Growth Factor βs are Upregulated in the Rat Masseter Muscle Hypertrophied by clenbuterol, a $β_2$ Adrenergic Agonist," (2006) British Journal of Pharmacology, vol. 147, pp. 412-421.
Ghoghawala, et al., "β2-Adrenergic Receptor Signaling Mediates Corneal Epithelial Wound Repair," Journal of Investigative Ophthalmology and Visual Science, May 2008, vol. 49, No. 5, pp. 1857-1863.
Gosain et al., "Nerepinephrine Modulates the Inflammatory and Proliferative Phases of Wound Healing," Journal of Trauma® Injury, Infection, and Critical Care, Apr. 2006, vol. 60(4), pp. 736-744.
Liu et al., "cAMP Inhibits Transforming Growth Factor-β-Stimulated collagen Synthesis via Inhibition of Extracellular Signal-Regulated Kinase ½ and Smad Signaling in Cardiac Fibroblasts," Molecular Pharmacology, (2006), vol. 70, pp. 1992-2003.
Martindale: The Complete Drug Reference $35^{th}$ Ed. (2007) Pharmaceutical Press, pp. 1014-1019.
Pullar et al., "β2-Adrenergic Receptor Activation Delays Dermal Fibroblast-Mediated Contraction of Collagen Gels via a cAMP-Dependent Mechanism," Wound Repair & Regeneration, (2005), vol. 13, pp. 405-411.
Pullar et al., "Cyclic AMP Mediates Keratinocyte Directional Migration in an Electric Field," Journal of Cell Science, (2005) vol. 118, pp. 2023-2034.
Pullar et al., "PP2A Activation by β2-Adrenergic Receptor Agonists," Journal of Biological Chemistry (2003), vol. 278, pp. 22555-22562.
Pullar et al., "β2-Adrenergic Receptor Activation Delays Wound Healing," FASEB Journal (2006), vol. 20, pp. 76-86.
Pullar et al., "β-Adrenergic Receptor Antagonists Accelerate Skin Wound Healing," Journal of Biological Chemistry (2006), vol. 281, pp. 21225-21235.
Pullar et al., "The β2-Adrenergic Receptor Activates Pro-Migratory and Pro-proliferative Pathways in Dermal Fibroblasts via Divergent Mechanisms," Journal of Cell Science (2006), vol. 119, pp. 592-602.
Pullar et al., "β-Adrenergic Receptor Agonists Delay While Antagonists Accelerate Epithelial Wound Healing," Journal of Cellular Physiology (2007), vol. 211(1), pp. 261-272.
Pullar et al (2008) "β-Adrenergic Receptor modulation of wound repair" in Pharmacological Research. In Press.
Souza et al., "Blockade of $β_1$-and $β_2$-Adrenoceptors Delays Wound Contraction and Re-Epithelialization in Rats," Clinical and Experimental Pharmacology and Physiology (2006), vol. 33, pp. 421-430.
Tanaka et al., "Quantitative Estimation of Myocardial Fibrosis Based on Receptor Occupancy for β2-Adrenergic Receptor Agonists," Journal of Toxicological Sciences (2004), vol. 29, No. 3, pp. 179-186.
Rasmussen et al., "Crystal Structure of the Human β2 Adrenergic G-Protein-Coupled Receptor," Nature Publishing Group (2007), vol. 450, pp. 383-387.
Redd et al., "Wound Healing and Inflammation: Embryos Reveal the Way to Perfect Repair," Phil. Trans. R. Soc. Lond. B. Biol. Sci. (2004), vol. 359, pp. 777-784.
Hinz et al., "Formation and Function of the Myofibroblast During Tissue Repair," Journal of Investigative Dermatology (2007), vol. 127, pp. 526-537.
Shah et al., "Neutralisation of TGF-$β_1$ and TGF-$β_2$ or exogenous addition of TGF-$β_3$ to Cutaneous Rat Wounds Reduces Scarring," Journal of Cell Science (1995), vol. 108, pp. 985-1002.
Van Zuijlen et al., "Scar Assessment Tools: Implications for Current Research," Plast. Reconstr. Surg. (2002), vol. 109, pp. 1108-1122.
International Preliminary Report on Patentability for International Application No. PCT/GB2009/000829 dated Sep. 28, 2010.
Sean C. Sweetman;—"Bronchodilators and Anti-asthma Drugs", Martindale The Complete Drug Reference Thirty-fifth edition, p. 997.

* cited by examiner

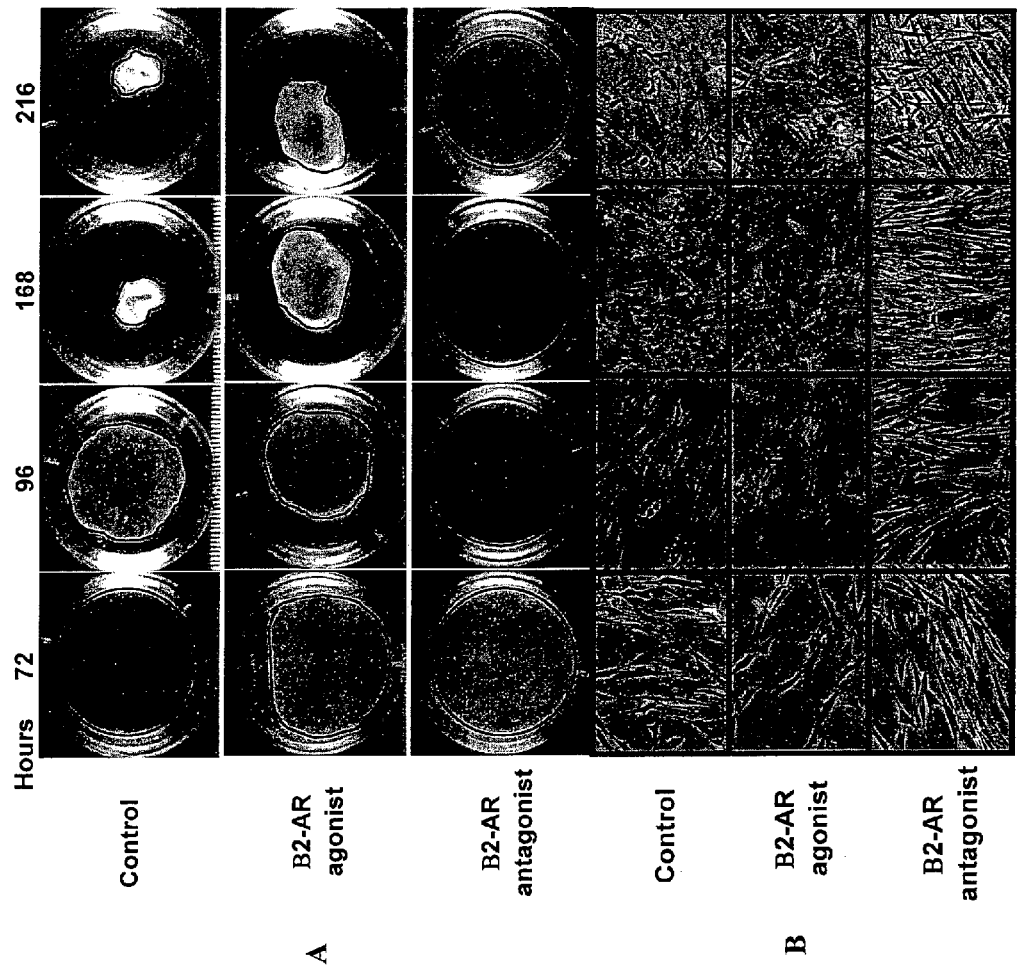
Figure 8 (1/2)

(2/2)

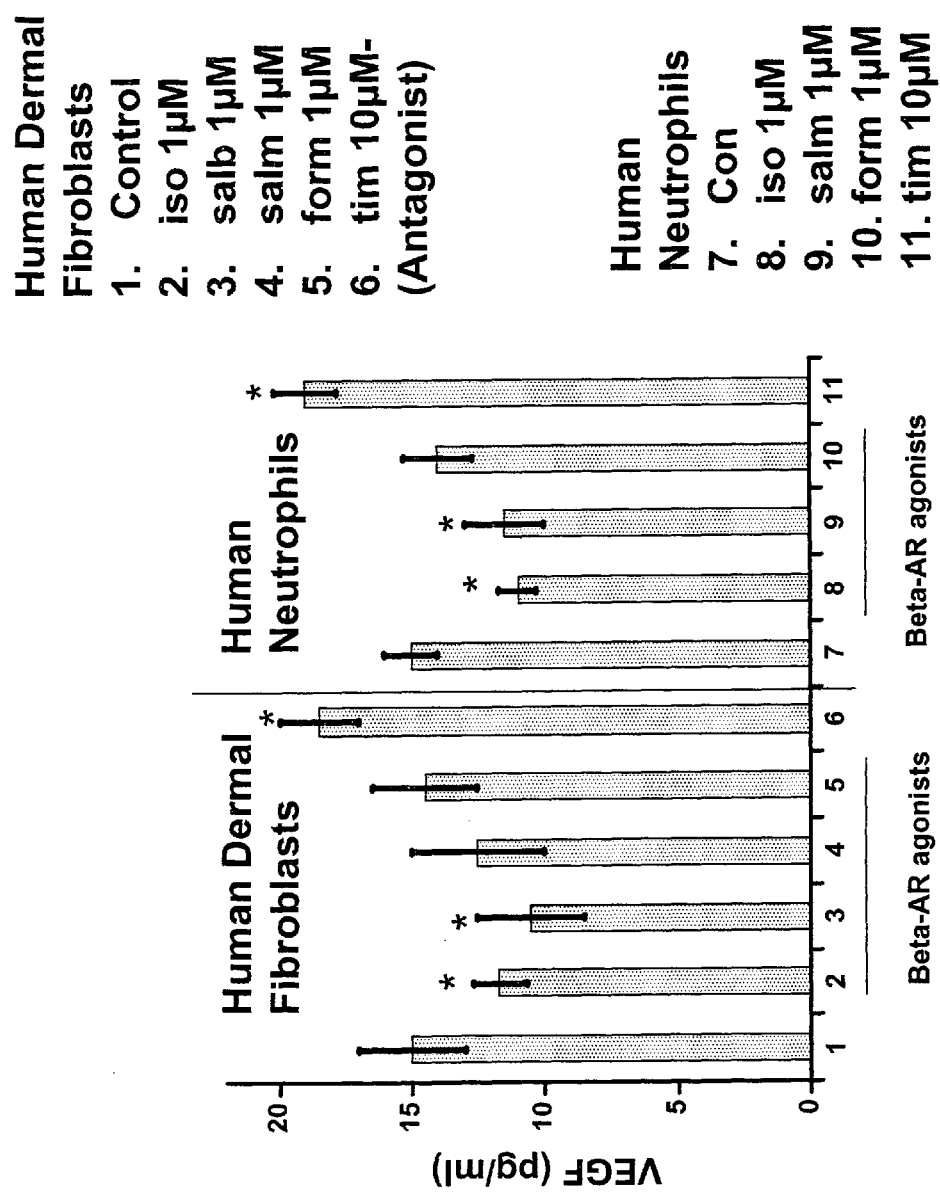

MODULATION OF FIBROBLAST ACTIVITY

PRIORITY CLAIM

This application claims priority to and the benefit of Intnl. Appl. No. PCT/GB2009/000829, entitled "Modulation Of Fibroblast Activity", filed Mar. 27, 2009, the entire contents of which are hereby incorporated by reference and relied upon.

The present invention relates to pharmaceutical compositions, medicaments and methods of treatment for use for simultaneously altering the amount of TGFβ1 and TGFβ3 produced by a fibroblast, and for altering fibroblast function, activity and differentiation. The invention also relates to the reduction or prevention of scar formation. The invention also relates to compositions, medicaments and methods for use in the treatment of fibrotic disorders, for use in altering collagen deposition, and for use in the treatment of wrinkles in the skin.

Fibroblasts are involved in many processes within the body. Wound healing is a complex process requiring the combined activation of numerous processes including the modulation of fibroblast activity. During the wound healing process, dermal fibroblasts migrate to the wound bed where wound cell-secreted Transforming Growth Factor-1 (TGF-β1), matrix molecules (eg a fibronectin splice variant) and mechanical cues (ie matrix tension) initiate their differentiation into myofibroblasts. Myofibroblasts can be distinguished from dermal fibroblasts as they express smooth muscle α-actin, contain bundles of contractile microfilaments, and have extensive cell-to-matrix attachment sites. The myofibroblasts synthesise, deposit and remodel the extracellular matrix to form granulation tissue, and thereby contract the wound. The connective tissue that forms during the healing process is often fibrous in nature, and commonly forms into a connective tissue scar by a process known as fibrosis.

In the embryo, healing processes are activated and halted to regenerate tissue perfectly, and so scarring may not occur. However, in the adult, evolution has optimised wound healing processes to achieve wound closure quickly, minimising the risk of infection, but resulting in scar formation. Viewed macroscopically, scars may be depressed below the surface of the surrounding tissue, or elevated above the surface of the undamaged skin. Scars may be relatively darker coloured than the unwounded tissue (hyperpigmentation) or may have a paler colour (hypopigmentation) than their surroundings. Either hyperpigmented or hypopigmented scars constitute a readily apparent cosmetic defect, and 100 million patients develop wound scars every year from elective operations, trauma, burn injuries and keloids. It has been shown that the cosmetic appearance of a scar is one of the major factors contributing to the psychological impact of wounds upon the sufferer, and that these effects can remain long after the wound itself has healed.

Excessive myofibroblast activity also produces the tissue deformations that are characteristic of fibrotic diseases. Accordingly, agents that could decrease fibroblast migration, proliferation or differentiation are thought to reduce wound scarring and fibrosis. In addition, a number of treatments that accelerate wound repair have also been shown to decrease fibrosis and scarring (Ha et al (2003) *Chin Med J (Engl)* 116, 1029-33; Huang et al (2002) *Faseb J* 16, 1269-70; Rodgers et al (2003) *J Invest Dermatol* 127, 526-37).

The pursuit of scarless healing has highlighted a number of differences between embryonic and adult wounds. In particular, embryonic wounds have decreased levels of TGF-β1 and TGF-β2, and increased levels of TGF-β3, exhibit no inflammatory response, and contain few myofibroblasts, thereby resulting in scarless wound repair. However, in contrast, adult wounds have increased levels of TGF-β1 and TGF-β2, and decreased levels of TGF-β3, exhibit inflammatory responses, and contain many myofibroblasts, thereby frequently resulting in scar formation during wound repair. It has previously been shown that reducing TGF-β1 levels at the adult wound site reduces scar formation. Furthermore, it has been shown that adding recombinant TGF-β3 to adult wounds reduces inflammation, matrix deposition and scarring.

At present, there is no pharmaceutical on the market for effectively reducing wound scarring, though Renovo have two potential treatments that are currently in clinical trials, ie Juvidex™ and Juvista™. Juvidex™ is a mannose-6-phosphate formulation that inhibits the actions of TGF-β1 and β2, whereas Juvista™ is a human recombinant TGF-β3. Juvidex™ is only currently in clinical trials for the treatment of corneal scarring, because it has to be used at very high doses to be therapeutically effective, and the only route where a sufficiently high dose may be administered is by eye drops to be added directly to the eye. Juvista™ has been shown to be effective at reducing scars if added at the time of wounding to a surgically clean wound. However, Juvista™ is very expensive.

WO 2006/108176 relates to β2 AR agonists and antagonists for modulating wound healing, wound contraction and/or epithelialization. Various uses of or observations on β2 AR agonists are disclosed in EP 1 719 507; WO 01/94319; WO 2007/137204; U.S. Pat. No. 5,958,432; WO 03/097073; WO 2006/027579; Eggleston et al (1991) *Chest* 99, 1088-1092; Barzon et al (1991) *Eur. Resp. J.* 19, 2307-2311; Skipsii et al (1991) *Terapevtiicheski Arkhiv* 63, 125-127; Pullar & Isseroff (2005) *Wound Rep. & Regen.* 13, 405-411; Puller et al (2006) *FASEB J.* 20, 76-86; and Akutsu et al (2006) *Br. J. Pharmacol.* 147, 412-421.

It is therefore an object of the present invention to overcome or mitigate one or more of the problems of the prior art, whether identified herein or elsewhere, and to provide compositions and medicaments, which may be used in methods for simultaneously altering the amount of TGFβ1 and TGFβ3 produced by a fibroblast, for altering fibroblast differentiation, for preventing or reducing scarring, for treating certain fibrotic disorders, for altering collagen deposition, and for the treatment of wrinkles in the skin. These methods involve the modulation of fibroblast differentiation, activity and/or function.

Previously, the inventor of the present invention demonstrated that β2-adrenergic receptor (β2-AR) agonists decrease keratinocyte migration in vitro (Pullar et al (2003) *J Biol Chem* 278, 22555-62), re-epithelialisation in ex vivo human skin (Pullar et al (2006) *Faseb J* 20, 76-86) and dermal-fibroblast mediated contraction of floating collagen gels (Pullar and Isseroff (2005) *Wound Repair Regen* 13, 405-11), which is a model for dermal homeostasis. Based on these findings, the inventor deduced that β2-AR agonists do not increase the rate of wound healing. The general understanding in the art is that an agent which does not increase the rate of wound healing is expected to have little or no effect on reducing or inhibiting scarring. Conversely, the skilled technician would expect an agent, which does increase the rate of wound healing, to also reduce or inhibit scarring, and other fibrotic disorders. Accordingly, based on the inventor's previous observations in which a β2-AR agonist was unable to increase the rate of wound healing, the skilled technician would expect the β2-AR agonist to have little or no effect on the reduction of scarring.

Therefore, the inventor investigated the effect of β2-AR antagonists on the rate of wound healing and scarring with the expectation that they would be able to reduce scarring. However, as shown in the accompanying Figures, contrary to her expectations, the inventor was surprised to observe that β2-AR antagonists were unable to reduce or prevent scarring. However, she found that β2-AR antagonists are able to modulate the activity of fibroblasts, and that β2-AR antagonists are able to increase the deposition of collagen (FIGS. 6 and 7). The inventor investigated the effect of β2-AR agonists on scarring, and was surprised to find that a selective β2-AR agonist (eg salbutamol) altered the amount of cytokines that are secreted by dermal fibroblasts compared to a control. In particular, as shown in FIG. 9, the inventor quite unexpectedly observed that the β2-AR agonist decreased the amount of TGF-β1 that was secreted from dermal fibroblasts, while simultaneously increasing the amount of TGF-β3 that was secreted from fibroblasts. Although she does not wish to be bound by any hypothesis, the inventor believes that this alteration in cytokine profile (ie decrease in TGF-β1 concentration and increase in TGF-β3 concentration) within the fibroblast decreases the rate of fibroblast differentiation within a wound, thereby decreasing the concentration of myofibroblasts in the wound. Previous studies have shown that reducing TGF-β1 levels and increasing TGF-β3 levels at the adult wound site results in a reduction in scar formation. Hence, the inventor believed that this dual effect obtained upon application of a single compound (ie the selective β2-AR agonist) would be therapeutically effective for the treatment of fibrotic disorders, for use in altering collagen deposition and for use in reducing scarring. The data in FIG. 9 also shows that a selective β2-AR antagonist simultaneously increases the secretion of TGF-β1 and TGF-β2 from dermal fibroblasts.

Furthermore, additional data demonstrated a β2-AR agonist-mediated decrease in murine skin wound closure (as shown in FIG. 3), and the inventor further postulates that a reduction in the concentration of wound myofibroblasts decreases myofibroblast-mediated matrix deposition, wound re-modelling, and hence scarring. It will be appreciated that scars are areas of fibrous tissue that replace normal tissue after injury by a process known as fibrosis. The inventor has also demonstrated that a β2-AR agonist decreases smooth muscle α-actin concentration in the dermis (as shown in FIGS. 4 and 5), and also decreases the amount of collagen deposition in the dermis (as shown in FIGS. 6 and 7). The inventor has also demonstrated that 62-AR agonists decrease the recruitment of inflammatory cells to wounds (FIGS. 10 to 14) and that β2-AR agonists decrease the amount of VEGF, while β2-AR antagonists increase the amount of VEGF, secreted by dermal fibroblasts and neutrophils. Therefore, the inventor believes that a β2-AR agonist may also be harnessed for the treatment or prevention of particular fibrotic disorders and that modulators of β2-AR can simultaneously modulate the expression of TGFβ1 and TGFβ3 produced by a fibroblast, modulate fibroblast differentiation, activity and function and modulate collagen deposition.

A first aspect of the invention provides a method for simultaneously decreasing the amount of TGFβ1 and increasing the amount of TGFβ3 produced by a fibroblast, the method comprising contacting the fibroblast with an agent which positively modulates β2-adrenergic receptor.

A second aspect of the invention provides a method for simultaneously increasing the amount of TGFβ1 and TGFβ2 produced by a fibroblast, the method comprising contacting the fibroblast with an agent which negatively modulates β2-adrenergic receptor.

Before the present invention it had not been appreciated that modulation of the β2-AR could alter simultaneously the amount of TGFβ1 and TGFβ3 produced by a fibroblast and it had also not been appreciated that agents which modulate β2-AR could influence processes involved in fibroblast differentiation to myofibroblasts, VEGF secretion (VEGF being involved in angiogenic processes that may be associated with fibrotic disease), and collagen deposition.

A third aspect of the invention provides a method for reducing fibroblast differentiation, the method comprising contacting the fibroblast with an agent which positively modulates β2-adrenergic receptor.

A fourth aspect of the invention provides a method for increasing fibroblast differentiation, the method comprising contacting the fibroblast with an agent which negatively modulates β2-adrenergic receptor.

The myofibroblast is a key player in both the physiological reconstruction of connective tissue in the dermis after injury and the pathophysiological events that lead to tissue fibrosis. The differentiation of the fibroblast to the myofibroblast is a two-step process: Initially, within a few days of wounding, non-motile "quiescent" fibroblasts in the dermis acquire a migratory phenotype by up-regulating the expression of stress fibres, contractile bundles that allow the fibroblasts to generate small traction forces to move into the wound dermis. The environment of the wound dermis additionally stimulates the "activated" fibroblasts to differentiate into myofibroblasts. The main stimuli for fibroblast differentiation are TGFβ1, a splice-variant of fibronectin in the dermis, (ED-A FN) and the mechanical tension in the wound dermis. TGFβ1 is the major pro-fibrotic cytokine known to date. These stimuli promote the expression of alpha smooth muscle actin (a-SMA), which becomes incorporated into the contractile bundles in the cell allowing the myofibroblasts to actively remodel the newly synthesised collagen etc to form the dermis of the healing wound. During normal wound healing, when repair is completed, the myofibroblasts in the dermis will die by apoptosis and remodeling will cease. In pathophysiological wound repair, the myofibroblasts continue to synthesise and remodel matrix resulting in hypertrophic scarring.

It is particularly preferred to decrease fibroblast differentiation by the use of an agent which positively modulates β2-AR, since this reduces the number of myofibroblasts in the wound dermis and therefore reduces collagen deposition and remodelling.

A fifth aspect of the invention provides a method of decreasing the amount of VEGF secreted by a fibroblast or a neutrophil, the method comprising contacting the fibroblast or neutrophil with an agent which positively modulates β2-adrenergic receptor.

A sixth aspect of the invention provides a method of increasing the amount of VEGF secreted by a fibroblast or a neutrophil, the method comprising contacting the fibroblast or neutrophil with an agent which negatively modulates β2-adrenergic receptor.

VEGF is the major promoter of angiogenesis in the wound. Chronic wounds have reduced angiogenesis and VEGF can accelerate healing in chronic wounds but also increase scarring.

In the foregoing aspects of the invention it is preferred that the fibroblast is a dermal fibroblast. It is preferred that the fibroblast is present in an animal (ie the method is carried out on the animal). It is preferred that the animal is a human.

Typically, the fibroblast is present at a wound site. Also, typically, the fibroblast is present at a site of fibrotic disease.

A seventh aspect of the invention provides a method of simultaneously decreasing the amount of TGFβ1 and increasing the amount of TGFβ3 at a wound site, the method comprising administering to the wound site an agent which positively modulates β2-adrenergic receptor and an eighth aspect of the invention provides a method of simultaneously increasing the amount of TGFβ1 and TGFβ2 at a wound site, the method comprising administering to the wound site an agent which negatively modulates β2-adrenergic receptor.

A ninth aspect of the invention provides a method of reducing the deposition of collagen in a subject, the method comprising administering to the subject an agent which positively modulates β2-adrenergic receptor and a tenth aspect of the invention provides a method of increasing the deposition of collagen in a subject, the method comprising administering to the subject an agent which negatively modulates β2-adrenergic receptor.

One of the most visible changes associated with the aging process in humans relates to a progressive thinning of the skin and the appearance of coarse and fine wrinkles. The mechanism of wrinkle formation appears to involve changes to components of the dermal extracellular matrix including loss of collagen I deposition. Skin laxity, rhytides, and photoaging are generally treated by ablative procedures that injure or destroy the epidermis and its basement membrane, at least in the beginning, and subsequently lead to fibrosis of the papillary dermis. The ideal treatment would be to preserve the epidermis and promote normal collagen and elastin formation in the dermis. We have demonstrated that a β2-AR antagonist promotes dermal fibroblast-mediated collagen deposition (FIGS. 6 and 7). Thus, application of β2-AR antagonist, particularly its topical application would promote collagen deposition, restoring skin elasticity and reducing the appearance of fine lines and wrinkles, thus providing a means for combating or reducing wrinkles. Thus, the invention includes a method of combating or reducing wrinkling in the skin of an individual, the method comprising administering an agent which negatively modulates β2-AR (particularly a β2-AR antagonist) to the subject. Preferably, the agent, such as a β2-AR antagonist, is applied to the wrinkled skin.

In a further aspect, there is provided a method for preventing, reducing or inhibiting (collectively "combating") scarring, or for treating, ameliorating or preventing (collectively "combating") a fibrotic disorder, in a subject, the method comprising administering, to a subject in need of such treatment, a therapeutically effective amount of an agent, which positively modulates β2-adrenergic receptor conformation, or receptor activity, or activation thereof.

The inventor's findings that an agent, which positively modulates β2-AR (such as a β2-AR agonist), reduces scarring and fibrotic disorders were unexpected for two reasons. Firstly, the observation is in contrast to the general understanding in the technical field, which suggests that a negative modulator of β2-AR should in fact reduce scarring, and that a positive modulator should have no effect on scarring. Accordingly, the skilled technician would not have expected a positive modulator to be effective for reducing scarring or for treating fibrotic disorders. Secondly, the skilled technician would not have expected that the positive modulator of β2-AR would decrease the concentration of TGF-β1 concentration as well as simultaneously increasing the concentration of TGF-β3. As noted above, there is nothing in the prior art that would indicate that an agonist of β2-AR would fortuitously modulate TGF-β1 and TGF-β3 levels simultaneously.

Moreover, β2-AR modulators for use in the methods of the invention are known to be safe and well-tolerated in man. No adverse effects were observed in the in vivo experiments described in the Examples using the positive modulator, other than slowing down wound repair. Furthermore, modulators of β2-AR are cheap and easy to manufacture.

The skilled technician will appreciate what is meant by the term "β2-adrenergic receptor" or "β2-AR". These receptors are known in the art and have been reviewed in Johnson M, (*J Allergy Clin. Immunol.* (2006) 117, 18-24). However, for the avoidance of doubt, adrenergic receptors are a class of G protein-coupled receptors which bind and are activated by their endogenous ligands, the catecholamines, adrenaline and noradrenaline. The adrenergic receptors fall into 5 types: α1, α2, β1, β2, and β3, and the present invention is concerned with the β2-adrenergic receptor (ie β2-AR). The DNA and protein sequences for the human β2-adrenergic receptor are available on freely accessible databases and are discussed in Kobilka et al (1987 *PNAS* 84, 46-50). The chromosomal location for the gene encoding the β2-adrenergic receptor is chromosome Sq 31-32. Additionally, the crystal structure for the β2-AR is available (Rasmussen S et al *Nature* (2007) 450, 383-387).

By the term "positively modulate β2-adrenergic receptor conformation", we mean the agent (or modulator) is capable of altering the three-dimensional shape and configuration of the receptor from its inactive to active conformation.

Preferably, the agent, which positively modulates β2-AR in accordance with the invention, is capable of selectively modulating the β2-adrenergic receptor conformation, or receptor activity, or activation thereof. Hence, the agent is a β2-AR-selective positive modulator.

By the term "selectively modulate", we mean that the agent alters β2-AR conformation, or enhances or blocks the β2-AR activity, or activation thereof (as the case may be depending on whether the agent is a positive or negative modulator) to a greater extent, or at lower doses, than other types of adrenergic receptors, ie α1-, α2-, β1-, or β3-adrenergic receptors. Hence, it is preferred that the agent is selective for the β2-adrenergic receptor. It will be appreciated that a β-blocker inhibits the β1-, β2-, and β3-adrenergic receptors to similar extents, and so does not selectively inhibit the β2-adrenergic receptor. Similarly, α-blockers inhibit both the α1- and α2-adrenergic receptors, and so do not selectively inhibit the 2-adrenergic receptor.

The agent, which positively modulates β2-AR, may be capable of:—
  (i) altering the conformational state of the receptor, for example by stabilizing the active conformation of the receptor and/or maintaining the receptor in its active conformation to thereby allow the receptor to bind its natural ligand, ie the catecholamines;
  (ii) binding to the β2-adrenergic receptor, and increasing, promoting or augmenting transmission at the receptor;
  (iii) promoting or activating the downstream signalling pathways activated by the modulator binding to the receptor;
  (iv) increasing, promoting or augmenting transcription, translation or expression of the β2-adrenergic receptor;
  (v) increasing synthesis or release of the β2-adrenergic receptor, or agonists thereof, from intracellular stores; or (vi) decreasing the rate of degradation of β2-adrenergic receptor, or agonists thereof.

It will be appreciated that each of mechanisms (i) to (vi) results in altering transmission at the receptor, and hence the activity thereof, to thereby positively modulate the β2-adrenergic receptor.

Agents which negatively modulate β2-AR are likewise known and generally have the opposite of the effects of the agents which positively modulate β2-AR.

As indicated herein, the skilled technician would not expect that the agent, which positively modulates β2-AR, would decrease the concentration of TGF-β1 concentration as well as simultaneously increasing the concentration of TGF-β3 secreted from fibroblasts. Suitably, the agent, which positively modulates β2-AR, is capable of decreasing the concentration of TGF-β1 secreted from fibroblasts by at least 5%, more suitably at least 10%, even more suitably at least 15%, and still more suitably at least 20% compared to the concentration of TGF-β1 that would be secreted from fibroblasts in the absence of the positive modulator. Preferably, the agent, which positively modulates β2-AR, is capable of decreasing the concentration of TGF-β1 secreted from fibroblasts by at least 25%, more preferably at least 30%, even more preferably at least 35%, and still more preferably at least 40% compared to the concentration of TGF-β1 that would be secreted from fibroblasts in the absence of the positive modulator. It is especially preferred that the agent, which positively modulates β2-AR, is capable of decreasing the concentration of TGF-β1 secreted from fibroblasts by at least 45%, more preferably at least 50%, and still more preferably at least 55% compared to the concentration of TGF-β1 that would be secreted from fibroblasts in the absence of the positive modulator.

Suitably, the agent, which positively modulates β2-AR, is capable of increasing the concentration of TGF-β3 secreted from fibroblasts by at least 25%, more suitably at least 50%, even more suitably at least 100%, and still more suitably at least 125% compared to the concentration of TGF-β3 that would be secreted from fibroblasts in the absence of the positive modulator. Preferably, the agent, which positively modulates β2-AR, is capable of increasing the concentration of TGF-β3 secreted from fibroblasts by at least 150%, more preferably at least 175%, even more preferably at least 200%, and still more preferably at least 225% compared to the concentration of TGF-β3 that would be secreted from fibroblasts in the absence of the positive modulator. It is especially preferred that the agent, which positively modulates β2-AR, is capable of increasing the concentration of TGF-β3 secreted from fibroblasts by at least 250%, more preferably at least 275%, and still more preferably at least 300% compared to the concentration of TGF-β3 that would be secreted from fibroblasts in the absence of the positive modulator. As shown in FIG. 9, the inventor quite unexpectedly observed that the β2-AR agonist decreased the amount of TGF-β1 that was secreted from dermal fibroblasts by four fold, while simultaneously increasing the amount of TGF-β3 that was secreted from fibroblasts by five fold. It will be appreciated that the positive modulator for the β2-adrenergic receptor may be adapted to modulate the concentrations of TGF-β1 and TGF-β3 to any degree as set out herein, for example reducing the concentration of TGF-β1 by any of 5%, 10%, 15%, 20% and so on, and increasing the concentration of TGF-β3 by any of 25%, 50%, 75% and so on, preferably in vivo.

As shown in FIG. 9, the inventor quite unexpectedly observed that the β2-AR antagonist increased the amount of TGF-β1 that was secreted from dermal fibroblasts by three fold, while simultaneously increasing the amount of TGF-β2 that was secreted from dermal fibroblasts by 1.6 fold.

It will also be appreciated that the negative modulator for the β2-adrenergic receptor may be adapted to modulate concentrations of TGF-β1 and TGF-β2 to any degree as set out herein, for example increasing the concentration of TGF-β1 and TGF-β2 by any of 5%, 10%, 15%, 20% and so on, preferably in vivo.

Suitably, the binding affinity value (Ki value) of the positive or negative modulator for the β2-adrenergic receptor is less than about 100 nM, more suitably less than 80 nM, and more suitably less than 50 nM. Preferably, the Ki value of the positive or negative modulator for the β2-adrenergic receptor is less than 30 nM, more preferably less than 15 nM, and more preferably less than 10 nM.

A preferred agent, which positively modulates β2-AR, is a β2-adrenergic receptor agonist.

By the term "agonist", we mean a molecule that selectively binds to the β2-adrenergic receptor to initiate the signal transduction reaction.

A suitable agonist may be selected from a list of agonists consisting of a simple chemical organic or inorganic compound; a peptide; a protein; a nucleic acid; a sugar; an antibody (or an active fragment thereof); or any other biological or chemical agent; each of which is capable of altering receptor conformation/stability, or inducing the receptor's activity.

Suitable β2-adrenergic receptor agonists may include fenoterol, butoxamine, salbutamol, clenbuterol, formoterol, or salmeterol. However, a preferred β2-adrenergic receptor-selective agonist is salbutamol, as described in the Examples. Salbutamol is a highly selective β2-AR agonist, and will be known to the skilled technician.

The log $K_d$ (dissociation constant) of salbutamol for β1 is −4.66, for β3 is −4.33, and for β2 is −6.12. Hence, the log $K_d$ is much lower for β2-adrenergic receptor than for the β1- or the β3-AR. Salbutamol is therefore at least 29 times more selective for β2-AR than for the β1-AR, and 62 times more selective for β2-AR than for the β3-AR, and may therefore be described as being a β2-AR-selective agonist.

A preferred agent for use in those aspects of the invention that require a negative modulator of β2-AR is a β2-adrenergic receptor antagonist.

By the term "antagonist", we mean a molecule that selectively binds to the β2-adrenergic receptor to block the signal transduction reaction.

Suitable β2-adrenergic receptor antagonists include ICI 118,551, timolol, labetalol, dilevelol, propanolol, carvedilol, nadolol, carteolol, penbutolol and sotalol. ICI 118,551 is preferred.

The invention also includes an agent which positively modulates β2-adrenergic receptor for use in simultaneously decreasing the amount of TGFβ1 and increasing the amount of TGFβ2 produced by a fibroblast or a neutrophil; for reducing fibroblast differentiation; for decreasing the amount of VEGF secreted by a fibroblast; for simultaneously decreasing the amount of TGFβ1 and increasing the amount of TGFβ3 at a wound site; for reducing the deposition of collagen in a subject; for combating a fibrotic disorder in an individual wherein the fibrotic disorder is any one of cirrhosis of the liver; idiopathic pulmonary fibrosis; fibrosis following myocardial infarction; CNS fibrosis following a stroke, or neurodegenerative disorders (eg Alzheimer's Disease, multiple sclerosis); proliferative vitreoretinopathy (PVR) and arthritis; adhesions, eg in the digestive tract, abdomen, pelvis, spine; nephrogenic systemic fibrosis; myocardial fibrosis; liver/hepatic fibrosis;

epidural fibrosis (failed back surgery syndrome); endomyocardial fibrosis; tubulointerstitial fibrosis; renal interstitial fibrosis; mediastinal fibrosis; retroperitoneal fibrosis; penile fibrosis; oral submucous fibrosis; kidney fibrosis; idiopathic pulmonary upper lobe fibrosis (Amitani disease); congenital hepatic fibrosis; postlaminotomy fibrosis; painful disc fibrosis; graft fibrosis; atrial fibrosis; corneal subepithelial fibrosis; congenital orbital fibrosis; bone fibrosis; peritoneal fibrosis; nephrogenic systemic fibrosis; non-cirrhotic portal fibrosis; pulmonary tuberculosis, disease-related pulmonary apical fibrosis in ankylosing spondylitis; colorectal fibrosis; periglomerular fibrosis/atubular glomeruli; basal fibrosis syndrome (emphysema/fibrosis syndrome); tissue fibrosis; and massive neck fibrosis; or for combating a fibrotic disorder in an individual wherein the fibrotic disorder is characterized by the result of trauma, iatragenesis or genetic susceptibility (excluding cystic fibrosis).

The invention also includes an agent which negatively modulates β2-adrenergic receptor for use in simultaneously increasing the amount of TGFβ1 and TGFβ2 produced by a fibroblast; for increasing fibroblast differentiation; for increasing the amount of VEGF secreted by a fibroblast or a neutrophil; for simultaneously increasing the amount of TGFβ1 and TGFβ2 at a wound site; or for increasing the deposition of collagen in a subject.

The invention also includes use of an agent which positively modulates β2-adrenergic receptor in the manufacture of a medicament for use in simultaneously decreasing the amount of TGFβ1 and increasing the amount of TGFβ2 produced by a fibroblast; for reducing fibroblast or neutrophil differentiation; for decreasing the amount of VEGF secreted by a fibroblast; for simultaneously decreasing the amount of TGFβ1 and increasing the amount of TGFβ3 at a wound site; for reducing the deposition of collagen in a subject; for combating a fibrotic disorder in an individual wherein the fibrotic disorder is any one of cirrhosis of the liver; idiopathic pulmonary fibrosis; fibrosis following myocardial infarction; CNS fibrosis following a stroke, or neurodegenerative disorders (eg Alzheimer's Disease, multiple sclerosis); proliferative vitreoretinopathy (PVR) and arthritis; adhesions, eg in the digestive tract, abdomen, pelvis, spine; nephrogenic systemic fibrosis; myocardial fibrosis; liver/hepatic fibrosis; epidural fibrosis (failed back surgery syndrome); endomyocardial fibrosis; tubulointerstitial fibrosis; renal interstitial fibrosis; mediastinal fibrosis; retroperitoneal fibrosis; penile fibrosis; oral submucous fibrosis; kidney fibrosis; idiopathic pulmonary upper lobe fibrosis (Amitani disease); congenital hepatic fibrosis; postlaminotomy fibrosis; painful disc fibrosis; graft fibrosis; atrial fibrosis; corneal subepithelial fibrosis; congenital orbital fibrosis; bone fibrosis; peritoneal fibrosis; nephrogenic systemic fibrosis; non-cirrhotic portal fibrosis; pulmonary tuberculosis, disease-related pulmonary apical fibrosis in ankylosing spondylitis; colorectal fibrosis; periglomerular fibrosis/atubular glomeruli; basal fibrosis syndrome (emphysema/fibrosis syndrome); tissue fibrosis; and massive neck fibrosis; or for combating a fibrotic disorder in an individual wherein the fibrotic disorder is characterized by the result of trauma, iatragenesis or genetic susceptibility (excluding cystic fibrosis).

The invention also includes use of an agent which negatively modulates β2-adrenergic receptor in the manufacture of a medicament for use in simultaneously increasing the amount of TGFβ1 and TGFβ2 produced by a fibroblast; for increasing fibroblast differentiation; for increasing the amount of VEGF secreted by a fibroblast or a neutrophil; for simultaneously increasing the amount of TGFβ1 and TGFβ2 at a wound site; or for increasing the deposition of collagen in a subject.

It will be appreciated that the ability of the agents to have the described effects in relation to modulating the amount of TGFβ1 and TGFβ3 produced by a fibroblast, modulating fibroblast differentiation, modulating VEGF secretion by a fibroblast, and modulating deposition of collagen gives rise to many clinical uses in non-injured skin, for example treating eczema or psoriasis. A notable use, as described above, is the use of a negative modulator of β2-AR (eg a β2-antagonist) for reducing wrinkling of skin.

It will be appreciated that the ability of the medicaments and methods of the invention involving an agent which positively modulates β2-AR to treat fibrotic disorders and to reduce scarring mean that these methods and medicaments are of value in a wide range of clinical settings. The methods and medicaments according to the invention may be used to treat fibrotic disorders and/or reduce scarring as a result of many different types of injury. For example, the methods and medicaments of the invention may be used to treat fibrotic disorders and/or reduce scarring caused by penetrating wounds or non-penetrating wounds formed as a result of physical insults or injuries including (but not limited to): grazes, abrasions, surgical incisions, and other surgical procedures (particularly partial thickness grafts of tissues such as the skin), "burns" (which, except for where the context requires otherwise, may be considered to include tissue damage resulting from exposure to either high or low temperature, chemical agents or radiation), and other forms of trauma.

Although the utility of the medicaments and methods of the invention are particularly suited to treat fibrotic disorders and/or reduce scarring in dermal wounds, it will be appreciated that they may also be used to reduce scarring of wounds and/or treat fibrotic disorders in many other tissues. Scars produced by the healing of wounds in tissues other than the skin may also have highly detrimental effects. The scar may be internal or external, and may be on any part of the subject's body. Specific examples of such tissues include (but are not limited to) scars occurring as a result of wound healing in the central nervous system (eg following neurosurgery or penetrating injuries of the brain); scars occurring as a result of wound healing in the eye; scarring occurring as a result of acne; scarring in the heart (eg following surgery or myocardial infarction); scars occurring as a result of wound healing involving the abdomen or pelvis; scarring arising as a result of wound healing in the pelvis in the region of the fallopian tubes; scarring following injury to muscles; and scarring or fibrosis following injury to tendons and ligaments.

It is known that TGF-β1 promotes scarring during wound healing, and that TGF-β3 reduces scarring. Accordingly, because medicaments of the invention have been shown to surprisingly reduce TGF-β1 levels and simultaneously increase TGF-β3 levels in a fibroblast, scarring during wound healing can be avoided. This is particularly important when treating ophthalmological conditions as a scar on the eye will often result in loss of vision quality. Hence, medicaments of the invention may be used in the treatment of ophthalmological conditions, such as persistent epithelial defects, neurotrophic keratitis, bullous keratopathy, excision of lesions, such as tumour of conjunctiva, and in association with stem cell transplant surgery.

The inventor has found that agonism of β2-adrenergic receptor activity is particularly effective in the prevention or treatment of scars, for example a pathological scar. Hence, medicaments and methods according to the invention may be used for reducing the formation of a scar which may be selected from a group of scars consisting of keloid scars, hypertrophic scars and pterygium.

The methods and medicaments of the invention relating to agents which positively modulate β2-AR may be used in reducing scar formation, which may be associated with grafting procedures. Treatment using the methods and medicaments of the invention will be beneficial both at a graft donor site (where it can aid the re-establishment of a functional epithelial layer while reducing scar formation), and also at graft recipient sites (where the anti-scarring effects of the treatment reduce scar formation). The inventor believes that the methods and medicaments of the invention confer advantages in the contexts of grafts utilising skin, artificial skin, or skin substitutes.

Medicaments according to the invention relating to agents which positively modulate β2-AR may be applied to a wound site or a site which may result in scarring, as a graft or patch beside, underneath, or on top of the affected area and adjacent healthy tissue, as is amply described in the published literature. Hence, it should be appreciated that the agent, which positively modulates β2-AR (eg an agonist), may be applied directly to the site to be treated. Alternatively, the positive modulator may be processed into a suitable therapeutically acceptable composition for subsequent application, such as an oil, cream, aerosol, hydrogel or liquid, depending on the treatment site, as described herein.

The medicaments relating to agents which positively modulate β2-AR may be used during skin transplantation, or as a biological dressing for burned skin, skin wounds, and chronic ulcers, eg in the leg, as an adjunctive tissue in surgical reconstruction of artificial body parts, or to prevent tissue adhesion in surgical procedures of the abdomen, head, and pelvis.

The prevention or reduction of scarring within the context of the present invention should be understood to encompass any reduction in scarring as compared to the level of scarring occurring in a control-treated or untreated wound, ie one to which an agent, which positively modulates β2-AR, has not been administered. Although medicaments of the invention which positively modulate β2-AR may be used to reduce scarring of wounds and/or treat fibrotic disorders in the wide range of tissues described herein, it is preferred that they are used to reduce scarring of the skin. The reduction of dermal scarring achieved using methods and medicaments of the invention may be assessed with reference to either the microscopic and/or, preferably macroscopic, appearance of a treated scar as compared to the appearance of an untreated scar. More preferably, the reduction in scarring may be assessed with reference to both macroscopic and microscopic appearance of a treated scar. By the term "treated scar", we mean a scar formed on healing of a treated wound, whereas an "untreated scar" means the scar formed on healing of an untreated wound, or a wound treated with a placebo or standard care. Suitable comparison scars may preferably be matched to the treated scar with reference to scar age, site, size and patient.

In considering the macroscopic appearance of a scar resulting from a treated wound, the extent of scarring, and hence the magnitude of any reduction in scarring achieved, may be assessed with reference to any of a number of parameters. Suitable parameters for the macroscopic assessment of scars may include: (i) colour of the scar; (ii) height of the scar; (iii) surface texture of the scar; and (iv) the stiffness of the scar. A treated scar will preferably demonstrate a reduction in scarring as assessed with reference to at least one of the parameters for macroscopic assessment set out above. More preferably, a treated scar may demonstrate reduced scarring with reference to at least two of the parameters, even more preferably at least three of the parameters, and most preferably all four of these parameters.

Suitable parameters for the microscopic assessment of scars may include:—(i) thickness of extracellular matrix (ECM) fibres; (ii) orientation of ECM fibres; (iii) ECM composition of the scar; and (iv) the cellularity of the scar. A treated scar will preferably demonstrate a reduction in scarring as assessed with reference to at least one of the parameters for microscopic assessment set out above. More preferably, a treated scar may demonstrate reduced scarring with reference to at least two of the parameters, even more preferably at least three of the parameters, and most preferably all four of these parameters. A reduction or an improvement in scarring of a treated wound may further be assessed with reference to suitable parameters used in the:—
  i) macroscopic clinical assessment of scars, particularly the assessment of scars upon a subject;
  ii) assessment of photographic images of scars; and
  iii) microscopic assessment of scars, for example by histological analysis of the microscopic structure of scars.

It will be appreciated that an improvement in scarring of a treated wound may be indicated by improvement of one or more such suitable parameters, and that in the case of an improvement as assessed with reference to a number of parameters, that these parameters may be combined from different assessment schemes (eg improvement in at least one parameter used in macroscopic assessment and at least one parameter used in microscopic assessment). A reduction or improvement in scarring may be demonstrated by an improvement in one or more parameters indicating that a treated scar more closely approximates unscarred skin with reference to the selected parameter(s) than does an untreated or control scar.

Suitable parameters for the clinical measurement and assessment of scars may be selected based upon a variety of measures or assessments including those described by Beausang et al (1998, *Plast. Reconstr. Surg.* 102(6): 1954-1961) and van Zuijlen et al (2002, *Plast. Reconstr. Surg.* 109(3): 1108-22). An overall assessment of scarring may be made using, for example, a Visual Analogue Scale or a digital assessment scale. Hence, typically, suitable parameters may include: assessment with regard to Visual Analogue Scale (VAS) scar score, scar height, scar width, scar perimeter, scar area or scar volume, appearance and/or colour of scar compared to surrounding unscarred skin, scar distortion and mechanical performance, scar contour and scar texture, collagen organisation, fibre thickness and fibre density. Each of these parameters will be known to the skilled technician. A reduction or improvement in scarring may be demonstrated by a change in any of these parameters such that a potential wound site or a scar treated with the positive modulator of β2-AR more closely resembles unscarred skin than does a control or untreated scar.

It is preferred that the wound to be treated is one in which a decrease in wound contraction is not desired. This is in order to prevent or treat undesirable outcomes. Excessive wound contraction can cause unpleasant cosmetic effects, impairment of modility and discomfort due to increased tension across the wound site and occurs due to excessive contraction of existing tissues. These wounds are to be distinguished from the wounds to be addressed by this invention where adverse outcomes (eg scarring) are due to aberrant collagen deposition and/or remodelling.

It is preferred that the subject or individual is one who does not suffer from a lupus erythromatosus or scleroderma or systemic sclerosis.

It is preferred that the β2-AR agonist is not a molecule which also has phosphodiesterase-4 (PDE-4) activity.

It is preferred that the scar is not a hypertrophic scar.

It will be appreciated that scars are areas of fibrous tissue that replace normal tissue after injury by the process known as fibrosis. Hence, related to scarring, the skilled technician will be aware that fibrotic disorders are medical indications in which excessive fibrosis leads to pathological derangement and malfunctioning of tissue. Fibrotic disorders are characterised by the accumulation of fibrous tissue (predominantly collagens) in an abnormal fashion within the tissue. Accumulation of such fibrous tissues may result from a variety of disease processes. As shown in FIGS. 6 and 7, the inventor has demonstrated that β2-AR agonist-treated wounds contained less collagen III deposition than untreated control wounds. Therefore, in view of these data, the inventor believes that administration of an agent, which positively modulates β2-AR, may be used in the treatment, amelioration or prevention of fibrotic disorders.

Fibrotic disorders do not necessarily have to be caused by surgery, traumatic injury or wounding. Fibrotic disorders are usually chronic, and may be selected from a group consisting of cirrhosis of the liver; idiopathic pulmonary fibrosis; fibrosis following myocardial infarction; CNS fibrosis following a stroke, or neurodegenerative disorders (eg Alzheimer's Disease, multiple sclerosis); proliferative vitreoretinopathy (PVR) and arthritis; adhesions, eg in the digestive tract, abdomen, pelvis, spine; nephrogenic systemic fibrosis; myocardial fibrosis; liver/hepatic fibrosis; epidural fibrosis (failed back surgery syndrome); endomyocardial fibrosis; tubulointerstitial fibrosis; renal interstitial fibrosis; mediastinal fibrosis; retroperitoneal fibrosis; penile fibrosis; oral submucous fibrosis; kidney fibrosis; idiopathic pulmonary upper lobe fibrosis (Amitani disease); congenital hepatic fibrosis; postlaminotomy fibrosis; painful disc fibrosis; graft fibrosis; atrial fibrosis; corneal subepithelial fibrosis; congenital orbital fibrosis; bone fibrosis; peritoneal fibrosis; nephrogenic systemic fibrosis; non-cirrhotic portal fibrosis; pulmonary tuberculosis, disease-related pulmonary apical fibrosis in ankylosing spondylitis; colorectal fibrosis; periglomerular fibrosis/atubular glomeruli; basal fibrosis syndrome (emphysema/fibrosis syndrome); tissue fibrosis; and massive neck fibrosis. There is therefore a need for medicaments which may be used for the treatment of such conditions by regulating (ie preventing, inhibiting, or reversing) fibrosis/scarring in these fibrotic disorders.

It is preferred if the fibrotic disorder is not cystic fibrosis.

It is preferred if the fibrotic disorder is not a disorder of the lungs.

It is preferred if the fibrotic disorders are due to trauma, or are iatrogenic or are due to an underlying genetic predisposition (excluding cystic fibrosis), and not fibrotic disorders caused by long term exposure to chemical or physical irritants.

By "trauma" we include the result of an incident of accidental or intentional acute injury to tissue (eg surgical incisions).

By "iatrogenic" we include the result of a medical treatment or therapy (eg radiotherapy. By "fibrotic disorder characterized by genetic susceptibility" we include the result of an inherited predisposition to develop tissue fibrosis, excluding cystic fibrosis.

The inventor believes that the methods and medicaments of the invention relating to agents which positively modulate β2-AR are able to reduce scarring or may be used to treat fibrotic disorders when administered either prior to wounding, or once a wound has already been formed. The methods or medicaments of the invention may be used prophylactically, ie at sites where no wound exists, but where a wound that would otherwise give rise to a scar or chronic wound may be formed. By way of example, medicaments in accordance with the invention may be administered to sites that are to undergo wounding as a result of elective procedures (such as surgery, eg plastic surgery), or to sites that are believed to be at elevated risk of wounding. It may be preferred that the medicaments of the invention are administered to the site immediately prior to the forming of a wound (for example in the period up to six hours before wounding) or the medicaments may be administered at an earlier time before wounding (for example up to 48 hours before a wound is formed).

The skilled technician will appreciate that the most preferred times of administration prior to formation of a wound will be determined with reference to a number of factors, including the formulation and route of administration of the selected medicament, the dosage of the medicament to be administered, the size and nature of the wound to be formed, and the biological status of the patient (which may be determined with reference to factors such as the patient's age, health, and predisposition to healing complications or adverse scarring). The prophylactic use of methods and medicaments in accordance with the invention is one preferred embodiment of the invention, and is particularly preferred in the reduction of scarring in the context of surgical wounds.

The methods and medicaments of the invention are also useful to reduce scarring if administered after a wound has been formed. It is preferred that such administration should occur as early as possible after formation of the wound, but agents of the invention are able to reduce scarring at any time up until the healing process has been completed (ie even in the event that a wound has already partially healed, the methods and medicaments of the invention may be used to reduce scarring in respect of any remaining unhealed portion). It will be appreciated that the time-frame in which the methods and medicaments of the invention may be used to reduce scarring is dependent on the nature of the wound in question (including the degree of damage that has occurred, and the size of the wounded area). Thus, in the case of a large wound, the methods and medicaments of the invention may be administered relatively late in the healing response yet still be able to reduce scarring. The methods and medicaments of the invention may, for instance, preferably be administered within the first 24 hours after a wound is formed, but may still reduce scarring if administered up to two, three, four, five, six, seven, eight, nine or ten, or more, days after wounding.

The methods and medicaments of the invention may be administered on one or more occasions as may be necessary in order to reduce scarring or for treating fibrotic disorders. For instance, therapeutically effective amounts of the medicaments may be administered to a wound as often as required until the healing process has been completed to reduce the scarring process. By way of example, the medicaments of the invention may be administered daily or twice daily to a wound for at least the first three days following the formation of the wound.

Most preferably, the methods or medicaments of the invention may be administered both before and after formation of a wound. It will be appreciated that the amount of a medicament of the invention that should be applied to a wound depends on a number of factors such as the biological activity and bioavailability of the agent present in the medicament, which in turn depends, among other factors, on the nature of the 132-adrenergic receptor agonist, and the mode of administration of the medicament.

Generally, when medicaments in accordance with the invention are used to treat existing wounds, the medicament should be administered as soon as the wound has occurred (or in the case of wounds that are not immediately apparent, such as those at internal body sites, as soon as the wound has been diagnosed). Therapy with methods or medicaments in accordance with the invention should continue until the healing process has been accelerated, and scarring reduced, to a clinician's satisfaction.

It will be appreciated that the agent, which positively modulates $\beta 2$-AR, and medicaments according to the invention may be used in a monotherapy (ie use of an agent, which positively modulates $\beta 2$-AR conformation, or receptor activity or receptor activation alone), to reduce scarring or for treating fibrotic disorders. Alternatively, the agent, which positively modulates $\beta 2$-AR, and medicaments according to the invention may be used as an adjunct to, or in combination with, known therapies for reducing scarring or for treating fibrotic disorders. For example, when the agent or medicament is used for reducing scarring, it may be used in combination with known anti-scarring therapeutics, such as corticosteroid injections, cryotherapy, topical silicone sheets, radiation, pressure garments and Imiquimod (Meier K and Nanney L, B, *Expert Opinion in Emerging Drugs* (2006) 11(1), 39). When the agent or medicament is used for treating a fibrotic disorder, it may be used in combination with known anti-fibrotic compounds. Although few anti-fibrotic agents are in current use, stem cell therapies look promising as a treatment of cystic fibrosis (Sueblinvong et al (2007) *Clin. Chest Med.* 28(2), p 361). Furthermore, interferon gamma 1b (Bouros et al (2006) *Expert Opin. Biol. Ther.* 6(10), p 1051) and Pirfenidone (Antoniou (2006) *Expert Opin. Investig. Drugs* 15(7), p 823) hold promise as treatments for idiopathic pulmonary fibrosis. In addition, Bosentan, an endothelin 1 receptor blocker, could be a future treatment for systemic sclerosis (Jain and Varga (2006) *Expert Opin. Pharmacother* 7(11), p 1487).

Medicaments of the invention may be administered by any suitable route capable of achieving the desired effect, for example, of modulating TGF$\beta$1 and TGF$\beta$3 or TGF$\beta$1 and TGF$\beta$2 produced by a fibroblast or of modulating fibroblast differentiation, or of modulating the amount of VEGF secreted by a fibroblast or a neutrophil, or of modulating collagen deposition, or of reducing scarring or for reducing fibrotic disorders. In respect of scarring it is preferred that the medicaments are administered locally at the wound site or intended wound site. Hence, the agent, which modulates $\beta 2$-AR, and medicaments according to the invention may be combined in pharmaceutical compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a subject in need of treatment. It will be appreciated that the vehicle of medicaments according to the invention should be one which is well-tolerated by the subject to whom it is given.

Medicaments comprising the agent, which modulates $\beta 2$-AR, may be used in a number of ways. For instance, oral administration may be required, in which case the $\beta 2$-AR modulator may be contained within a composition that may, for example, be ingested orally in the form of a tablet, capsule or liquid. Compositions comprising the $\beta 2$-AR modulator may be administered by inhalation (eg intranasally).

Alternatively, or additionally, medicaments of the invention may be administered in a topical form for example positive $\beta 2$-AR modulators for use to reduce scarring or for the treatment of fibrotic disorders. Such administration may be effected as part of the initial and/or follow up care for the wounded area. The inventors believe that reduction of scarring or treatment of fibrotic disorders is particularly improved by topical application of a $\beta 2$-AR positive modulator to a wound (or, in the case of prophylactic application, to a tissue or site where a wound could be formed). Thus, for example, suitable medicaments may be in the form of a liquid, ointment, cream, gel, hydrogel, powder or aerosol. All of such compositions are suitable for topical application to a wound, which is a preferred means of administering the $\beta 2$-AR positive modulator to a subject (eg a person or animal) in need of treatment. It is preferred that such formulations are applied directly to a wound site, or at least adjacent a wound site. These means for topical application are also useful for administering a $\beta 2$-AR negative modulator, such as a $\beta 2$ antagonist, to the site of wrinkles on the skin.

Alternatively, the $\beta 2$-AR positive modulator or medicament may be provided on a vehicle (such as a sterile dressing or patch), which may be used to cover a wound site or site of aberrant fibrosis. It will be appreciated that the vehicle should be one that is well-tolerated by the patient and allows release of the active agent to the wound. Such a vehicle is preferably biodegradeable, bioresolveable, bioresorbable and/or non-inflammatory.

The $\beta 2$-AR positive or negative modulator used in accordance with the invention may also be incorporated within a slow or delayed release device. Such devices may, for example, be inserted on or under the skin, and the medicament may be released over days, weeks or even months. The device may be located at least adjacent the treatment site, eg directly on a wound site, or a site at which aberrant fibrosis is occurring. Preferably, the medicament is applied in and/or around a wound in order to reduce scarring or for treatment of a fibrotic disorder. Such devices may be particularly advantageous when long-term treatment with the $\beta 2$-AR positive or negative modulator is required and which would normally require frequent administration (eg at least daily injection).

In one embodiment, a pharmaceutically vehicle for administration of the $\beta 2$-AR positive or negative modulator may be a liquid, and a suitable pharmaceutical composition would be in the form of a solution. In another embodiment, the pharmaceutically acceptable vehicle is a solid, and a suitable composition of the medicament according to the invention is in the form of a powder or tablet. In a further embodiment, the $\beta 2$-AR positive or negative modulator may be formulated as a part of a pharmaceutically acceptable transdermal patch.

The inventors believe that optimum reduction of scarring may be effected by the administration of an agent, which positively modulates $\beta 2$-AR, by injection at or around the wound site. For instance, in the case of dermal wounds, the positive modulator of $\beta 2$-AR may be administered by means of intradermal injection. Thus, a preferred medicament in accordance with the invention comprises a solution of an agent, which positively modulates $\beta 2$-AR, which is injectable directly into a site requiring treatment (eg for injection around the margins of a site of epithelial damage or a site likely to be damaged). Hence, in a preferred embodiment, the medicament may be injected into a wound, or the site of an impending surgical incision. Injections may be intravenous (bolus or infusion) or subcutaneous (bolus or infusion), or intradermal (bolus or infusion). It is also envisaged that medicaments according to the invention may be administered systemically to a subject by injection into the blood stream.

Similarly, negative modulators of β2-AR, such as β2 antagonists may be injected at the site of wrinkles.

Medicaments of the invention comprising the β2-AR positive modulator are suitable to be used for reducing scarring or fibrotic disorders in the cornea. Corneal wounds may result from trauma to the eye arising as a result of accidental injury, or as a result of surgical operations (eg laser surgery on the cornea). In this case, a preferred medicament of the invention may be in the form of an eye drop.

Medicaments comprising the agent, which positively modulates β2-AR, may be used to treat external wounds, ie on an external surface. However, medicaments comprising the β2-AR positive modulator may also be used to treat internal wounds, ie wounds occurring within the body on an internal surface. Thus, for example medicaments in accordance with the invention may be formulated for inhalation (eg an aerosol) for use in wounds arising in the lungs or other respiratory epithelia.

It will be appreciated that the amount of the β2-AR positive modulator that is required is determined by its biological activity and bioavailability, which in turn depends on the mode of administration, the physicochemical properties of the agent and whether the agent is being used as a monotherapy or in a combined therapy. The frequency of administration will also be influenced by the above-mentioned factors and particularly the half-life of the agent within the subject being treated. Optimal dosages to be administered may be determined by those skilled in the art, and will vary with the particular agent in use, the strength of the pharmaceutical composition, the mode of administration, and the advancement of the scarring or fibrotic disease. Additional factors depending on the particular subject being treated will result in a need to adjust dosages, including subject age, weight, gender, diet, and time of administration.

Typically the amount of a β2-AR modulator required for use in the individual to effect the treatment will be within the range of 0.001 ng to 100 mg of the agent per 24 hours, although this figure may be modified upwards or downwards in response to the factors outlined above. For treatment of a wound site, the amount of the β2-AR positive modulator to be administered may preferably be 50 to 500 ng per linear centimeter of epithelial damage in the wound site. Generally, a daily dose of between 0.001 μg/kg of body weight and 10 mg/kg of body weight of the β2-AR positive modulator may be used for reducing scarring or treating fibrotic disorders depending upon which modulator is used. More preferably, the daily dose of the β2-AR positive modulator is between 0.01 μg/kg of body weight and 1 mg/kg of body weight, more preferably between 0.1 μg/kg and 100 μg/kg body weight, and most preferably between approximately 0.1 μg/kg and 10 μg/kg body weight.

Similar doses of β2-AR negative modulators may be used when they are indicated.

Frequency of administration will depend upon the biological half-life of the medicament used. Typically a cream or ointment containing the positive or negative modulator of β2-AR should be administered to a target tissue such that the concentration of the modulator at the treatment site, such as a wound (in the case of a positive modulator) is maintained at a level suitable for having a therapeutic effect. This may require administration daily, or even several times daily. Daily doses may be given as a single administration (eg a single daily injection). Alternatively, the β2-AR positive or negative modulator may require administration twice or more times during a day. As an example, the β2-AR positive or negative modulator may be administered as two (or more, depending upon the severity of the condition being treated) daily doses of between 0.07 μg and 700 mg (ie assuming a body weight of 70 kg). A patient receiving treatment may take a first dose upon waking and then a second dose in the evening (if on a two dose regime), or doses at 3- or 4-hourly intervals.

Alternatively, a slow or delayed release device may be used to provide optimal doses of the β2-AR positive or negative modulator to a patient without the need to administer repeated doses. Such devices may, for example, be placed on or inserted under the skin and the β2-AR positive modulator may be released over days, weeks or even months. Such a device may be particularly useful for patients (such as those suffering from chronic wounds) that require long-term reduction of scarring or treatment of fibrotic disorders. The devices may be particularly advantageous when used for the administration of a β2-AR positive modulator, which would normally require frequent administration (eg at least daily administration by other routes).

Known procedures, such as those conventionally employed by the pharmaceutical industry (eg in vivo experimentation, clinical trials, etc.), may be used to form specific formulations of the agents according to the invention and precise therapeutic regimes (such as daily doses of the agents and the frequency of administration). The inventor believes that she is the first to suggest that β2-AR modulators are capable of simultaneously modulating the concentrations of TGFβ1 and TGFβ3 produced by fibroblasts, and the applications of β2-AR modulators as herein disclosed.

Hence, in a further aspect of the invention, there is provided an anti-scarring composition comprising a therapeutically effective amount of an agent, which positively modulates β2-AR conformation, or receptor activity, or activation thereof, and optionally a pharmaceutically acceptable vehicle.

By the term "anti-scarring composition", we mean a pharmaceutical compound used in the therapeutic prevention, reduction or inhibition of scarring in a patient.

In a still further aspect, there is provided an anti-fibrotic composition comprising a therapeutically effective amount of an agent, which positively modulates β2-AR conformation, or receptor activity, or activation thereof, and optionally a pharmaceutically acceptable vehicle.

By the term "anti-fibrotic composition", we mean a pharmaceutical compound used in the therapeutic treatment, amelioration or prevention of a fibrotic disorder.

In a further aspect of the invention, there is provides an anti-wrinkle composition comprising a therapeutically effective amount of an agent which negatively modulates β2-AR, and optionally a pharmaceutically acceptable carrier.

The invention also provides in a further aspect, a process for making the composition according to the above aspects, the process comprising combining a therapeutically effective amount of an agent, which positively or negatively modulates β2-AR conformation, or receptor activity, or activation thereof (as the case may be), with a pharmaceutically acceptable vehicle.

The agent, which positively modulates β2-AR, in the composition according to the above aspects is preferably selective for β2-AR, and may be a β2-AR agonist. The agonist may be selected from a list of agonists consisting of a simple chemical organic or inorganic compound; a peptide; a protein; a nucleic acid; a sugar; an antibody (or an active fragment thereof); each of which are capable of altering receptor conformation/stability, or inducing the receptor's activity. The β2-AR-selective agonist may be fenoterol, butoxamine, salbutamol, clenbuterol, formoterol, or salmeterol. However, a preferred β2-AR-selective agonist in the composition is salbutamol.

The agent, which negatively modulates β2-AR, in the composition according to the above aspects is preferably selective for β2-AR, and may be a β2-AR antagonist. The antagonist may be from any of the chemical classes listed above for agonists. The β2-AR antagonists are any of ICI 118,551, timolol, labetalol, dilevelol, propanolol, carvedilol, nadolol, carteolol, penbutolol and sotalol. ICI 118,551 is preferred.

A "subject" may be a vertebrate, mammal, or domestic animal. Hence, medicaments according to the invention may be used to treat any mammal, for example livestock (eg a horse), pets, or may be used in other veterinary applications. Most preferably, the subject is a human being.

A "therapeutically effective amount" of agent is any amount which, when administered to a subject, results in a reduction of scarring in the subject, or which results in a reduction in the symptoms of a fibrotic disorder.

For example, the therapeutically effective amount of agent used may be from about 0.07 µg to about 700 mg, and preferably from about 0.7 µg to about 70 mg. It is preferred that the amount of agent is an amount from about 7 µg to about 7 mg, and most preferably from about 7 µg to about 700 µg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, in a preferred embodiment, the pharmaceutical vehicle is a liquid, and the pharmaceutical composition is in the form of a solution. Liquid vehicles are used in preparing solutions, suspensions, emulsions, syrups, elixirs and pressurized compositions. The active agent according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, eg cellulose derivatives, preferably sodium carboxymethyl cellulose solution), alcohols (including monohydric alcohols and polyhydric alcohols, eg glycols) and their derivatives, and oils (eg fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions which are sterile solutions or suspensions can be utilized by, for example, intramuscular, intrathecal, epidural, intraperitoneal, intravenous and particularly subcutaneous injection. The β2-AR positive or negative modulator may be prepared as a sterile solid composition that may be dissolved or suspended at the time of administration using sterile water, saline, or other appropriate sterile injectable medium.

The agents and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The agents used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

For a better understanding of the invention, and to show how embodiments of the same may be carried into effect, reference will now be made, by way of example, to the following Examples and accompanying Figures, in which:—

FIG. 1 is a bar chart demonstrating that a β2-AR antagonist increases dermal fibroblast single cell migration rate. "Speed" is the average speed in µm/min that the cells travel in a one-hour period of time. Statistical analysis was performed using the Student's T test (*$P<0.01$);

FIG. 2 is a graph showing that β2-AR antagonists enhance dermal 30 fibroblast-mediated floating collagen gel contraction. A solution of bovine collagen type I (97%) and type III was mixed with triple-strength DMEM, DMEM containing 20 mM Hepes buffer, calf serum, cells (detached by trypsin from monolayer confluent cultures), and in the presence (line is a combination of dashed and dots, ie "_ . . . _") or absence (solid black line) of 10 nM is 62-adrenoceptor antagonist (ICI 118,551);

FIG. 3 is a graph showing that a β2-AR antagonist enhances murine wound closure in vivo, whereas a β2-AR agonist delays wound closure. Wounds were treated topically with 100 µl of hydroactive gel alone (solid black line and circular symbols) or containing 0.1% selective β2-AR agonist (salbutamol, dotted line and square symbols) or 0.1% selective β2-AR antagonist (ICI 118,551, dashed line and diamond-shaped symbols) immediately after wounding and daily, thereafter until harvesting. Images were captured daily and wound area was calculated using Image J.

FIG. 4 are photographs showing that β2-AR antagonists increase the level of smooth muscle α-actin (SMA) staining in the wound dermis, 5 days post wounding, whereas β2-AR agonists decrease the level of smooth muscle α-actin staining in the wound dermis, 5 days post wounding. Images of SMA stained wound sections were captured at 2× magnification on a Nikon SMZ-U upright microscope with Nikon ACT-1 software, and representative images are shown. Scale bar is 500 μM;

FIG. 5 is a bar chart showing that β2-AR antagonists increase the level of smooth muscle α-actin staining in the wound dermis, 5 days post wounding, whereas β2-AR agonists decrease the level of smooth muscle α-actin staining in the wound dermis, 5 days post wounding;

FIG. 6 are photographs showing that β2-AR antagonists increase the amount of collagen III staining in the wound dermis, 5 days post wounding, whereas β2-AR agonists decrease the amount of collagen III staining in the wound dermis, 5 days post wounding. Images of the collagen III stained wound sections were captured at 20× magnification on a Nikon Eclipse 2000U inverted microscope with NIS-Elements software. Representative images are shown. Scale bar is 100 μM;

Panel A shows that β2-AR antagonist treatment increases the rigidity of human dermal fibroblast-seeded collagen gels after 4 days incubation. Human dermal fibroblasts were incorporated into tethered 40% collagen gels for 4 days, submerged in media alone or media containing 10 μM beta2-adrenoceptor agonist (salbutamol) or antagonist (ICI 118,551). Gels were incubated at 37° C. for up to 216 hours and photographed after 72, 96, 168 and 216 hours to observe the maintenance of tension in the gels.

Panel B shows that β2-AR agonist treatment decreases collagen I staining while antagonist treatment increases collagen I staining in human dermal fibroblasts released from collagen gels after 4 days incubation. Human dermal fibroblasts were incorporated into tethered collagen gels for 4 days, submerged in media alone or media containing 10 μM beta2-adrenoceptor agonist (salbutamol) or antagonist (ICI 118,551). Cells were released from the gels by treatment with collagenase, plated onto collagen 1-coated dishes, fixed with 4% paraformaldehyde and stained with an anti-collagen I antibody (black colouring).

Panel C shows that β2-AR agonist treatment decreases human dermal fibroblast proliferation while antagonist treatment increases cell proliferation in collagen gels after 4 days incubation. Human dermal fibroblasts were incorporated into tethered 40% collagen gels for 4 days, submerged in media alone or media containing 10 μM beta2-adrenoceptor agonist (salbutamol) or antagonist (ICI 118,551). Gels were incubated at 37° C. for 96 hours, photographed on an inverted Nikon microscope every 24 hours.

Panel D shows that β2-AR agonist treatment decreases smooth muscle alpha actin staining while antagonist treatment increases smooth muscle alpha actin staining in human dermal fibroblasts released from collagen gels after 4 days incubation. Human dermal fibroblasts were incorporated into tethered collagen gels for 4 days, submerged in media alone or media containing 10 μM beta2-adrenoceptor agonist (salbutamol) or antagonist (ICI 118,551). Cells were released from the gels by treatment with collagenase, plated onto collagen 1-coated dishes, fixed with 4% paraformaldehyde and stained with an anti-alpha smooth actin specific antibody.

Figure 9:
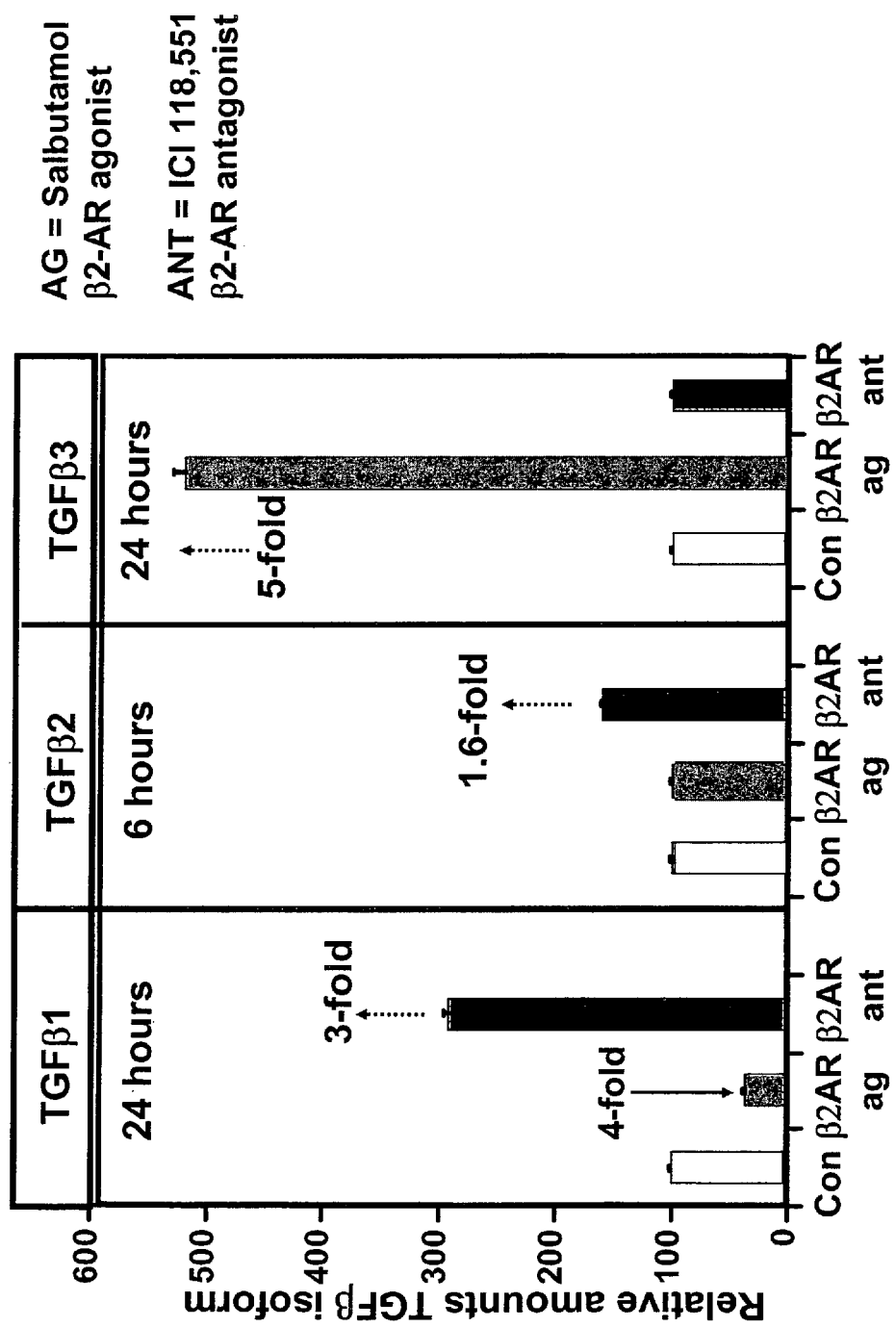

FIG. 9 shows that β2-AR agonists decrease the secretion of pro-fibrotic growth factors and increase the secretion of anti-fibrotic growth factors. Whereas, in contrast, β2-AR antagonists increase the secretion of pro-fibrotic growth factors, β2-AR agonists decrease the amount of secreted pro-fibrotic TGFβ1 by 74% and increase the amount of secreted anti-fibrotic TGFβ3 by 5 fold after 24 hours. In contrast, β2-AR antagonists increase pro-fibrotic TGFβ2 levels by 1.6 fold after 6 hours and increase TGFβ1 levels by 3 fold after 24 hours. Human dermal fibroblasts were plated in the presence or absence (control) of 10 μM beta2-adrenoceptor agonist (salbutamol) or antagonist (ICI 118,551). The supernatant was collected after 6 hours or 24 hours and analysed using individual ELISAs specific for TGFbeta 1, 2 or 3.

Figure 10:
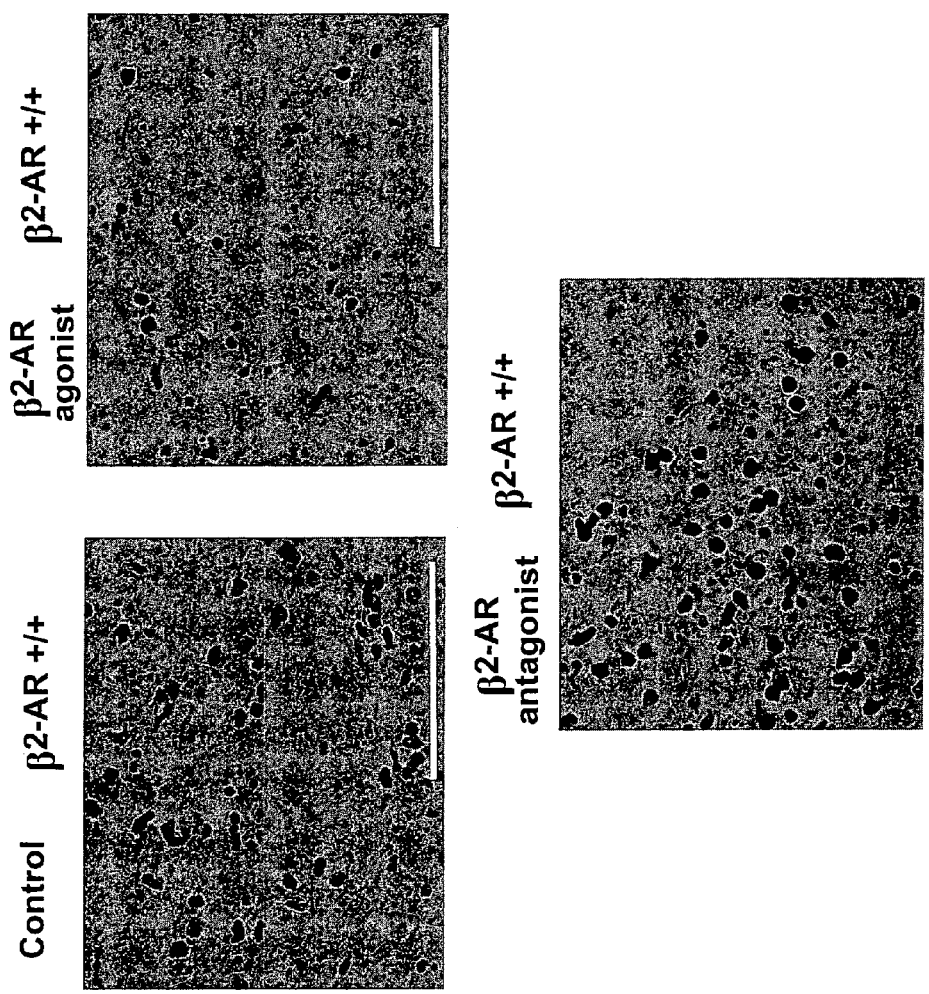
Figure 11:
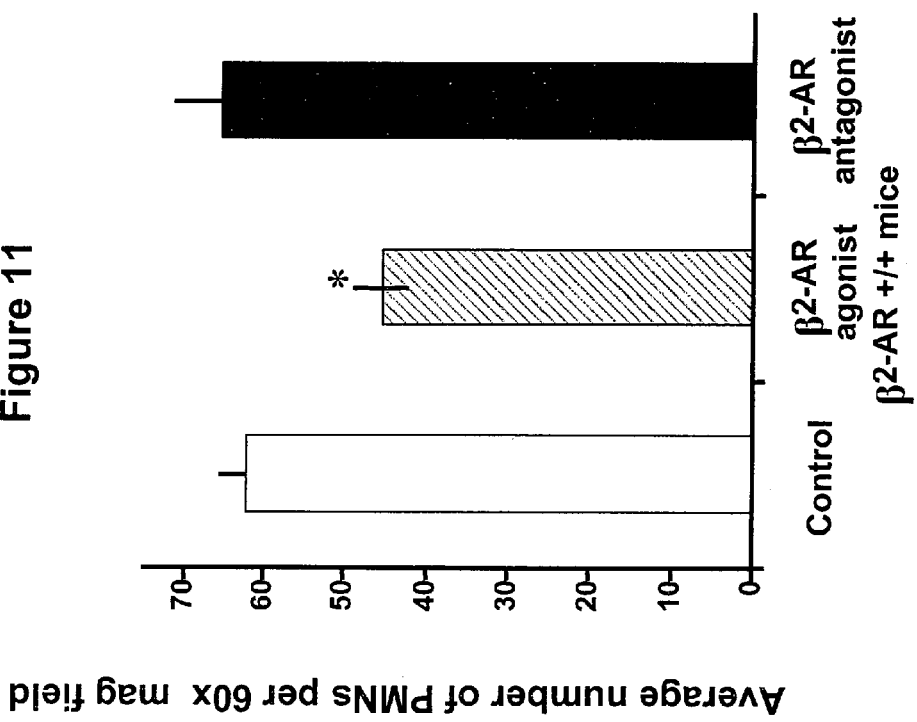
Figure 12:
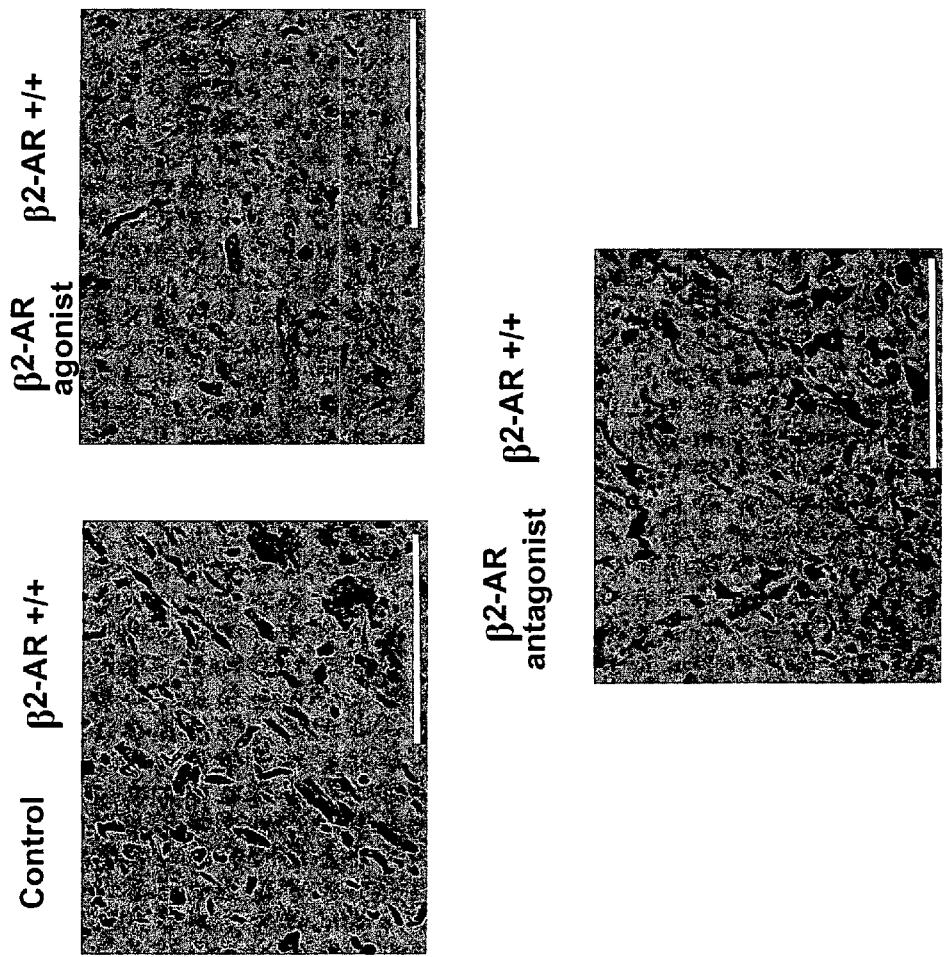
Figure 13:
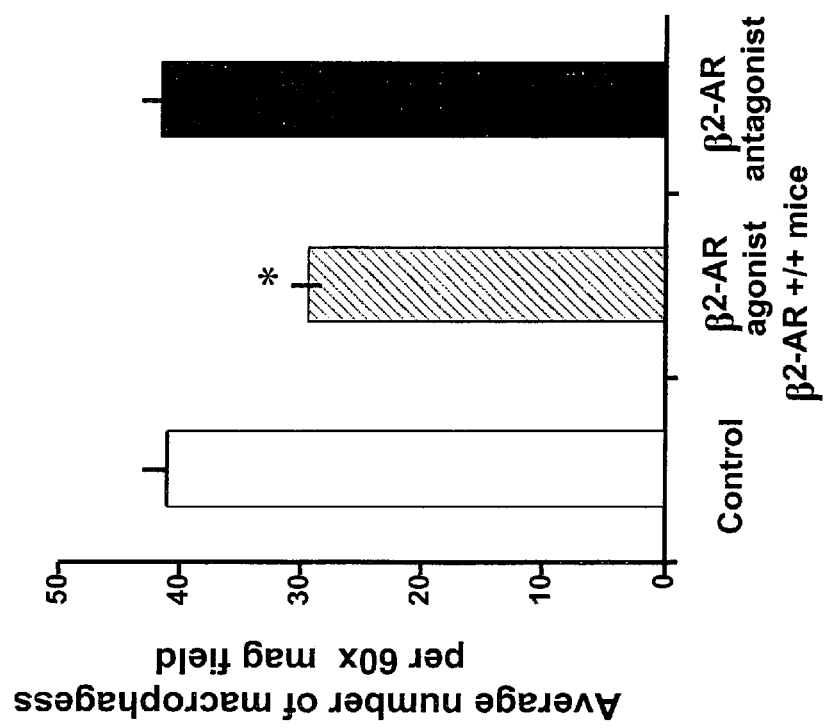

FIG. 10 are photographs showing that β2-AR agonists decrease the number of neutrophils in the wound bed after 3 days. Images of Ly6G-6C-stained wounds were captured at 60× magnification on a Nikon Eclipse 2000U inverted microscope with NIS-Elements software. Representative images are shown. Scale bar is 100 μM;

FIG. 11 is a bar chart showing that β2-AR agonists decrease the number of neutrophils (polymorphonuclear cells, PMNs) in the wound bed after 3 days;

FIG. 12 are photographs showing that β2-AR agonists decrease the number of macrophages in the wound bed after 3 days. Images of F 4/80-stained wounds were captured at 60× magnification on a Nikon Eclipse 2000U inverted microscope with NIS-Elements software. Representative images are shown. Scale bar is 100 μM; and FIG. 13 is a bar chart showing that β2-AR agonists decrease the number of macrophages in the wound bed after 3 days.

Figure 14:
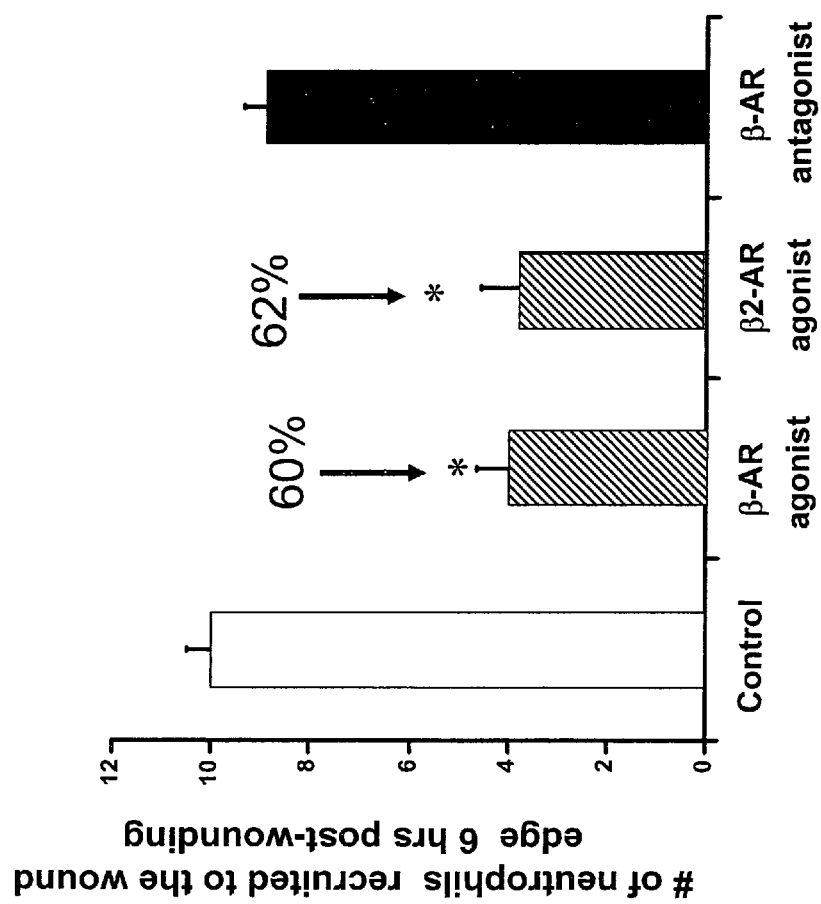

FIG. 14 shows that β and β2-AR agonists decrease the recruitment of inflammatory cells to zebrafish tail wounds, 6 hours post-wounding. The caudal fin of three day old zebrafish embryos was bisected with a scalpel to create a wound in the tail fin. The embryos were fixed in 4% paraformaldehyde 6 hours later and stained with fluorescein-tyramine to visualize the recruitment of neutrophils to the tail wounds on an inverted microscope at 20× magnification. Here is demonstrated that both β-AR and β2-AR agonists reduce neutrophil cell recruitment to zebra fish condal fin wounds by 60 and 62%, within 6 hours of wounding, respectively. In contrast, a β-AR antagonist has no effect (FIG. 14). This data reveals a novel β2-AR-mediated inhibition of neutrophil cell guidance to a wound. In addition, this is the first report of any physiological effect of a β2-AR agonist on zebrafish embryos.

FIG. 15 shows that β2-AR agonists decrease the amount of secreted pro-fibrotic VEGF while β2-AR antagonists increase pro-fibrotic VEGF levels secreted from human dermal fibroblasts and human neutrophils after 48 hours. Human dermal fibroblasts or neutrophils were plated in the presence or absence (control) of β-adrenoceptor agonists or antagonist. The supernatant was collected after 48 hours and analysed using an ELISA specific for VEGF. Iso is isoproterenol. Salb is salbutamol. Salm is salmeterol. Form is formotorol. Tim is timolol. Timolol is an antagonist, the other compounds are agonists.

EXAMPLES

Materials

The following experiments used a selective β2-adrenergic receptor agonist, salbutamol (Sigma-Aldrich, St Louise, Mo.). This compound is a highly selective β2-adrenergic receptor agonist, having Ki values of −6.12, −4.66, and −4.33 nM for β2-, β1-, and β3-adrenergic receptors, respectively. The experiments also used a selective β2-adrenergic receptor antagonist, ICI 118,551 (Tocris Cookson, Inc, Ellisville, Mo.). This compound is a highly selective β2-adrenergic receptor antagonist, having Ki values of 1.2, 120, and 257 nM for β2-, β1-, and β3-adrenergic receptors, respectively (Bilski et al (1983) *J. Cardiovasc. Pharmacol* 5, 430).

Methods

Single Cell Migration Assay

Figure 1:
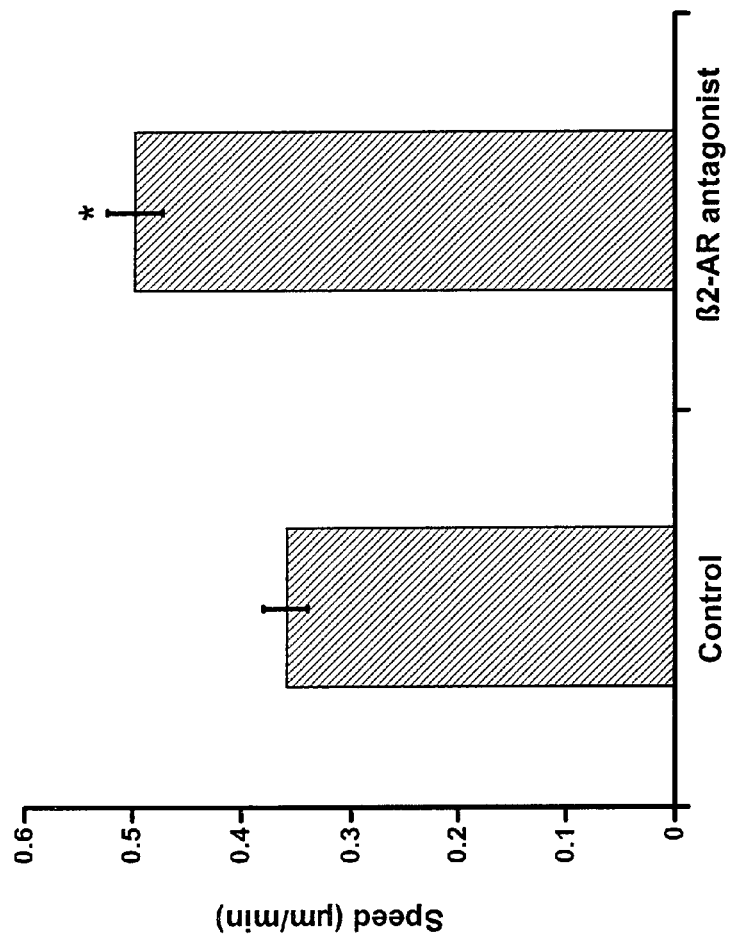

Glass bottomed 35 mm dishes (MatTek Corporation), were coated with collagen I (60 μg/ml) (Cohesion Technologies) in phosphate buffered saline (PBS) for 1 hour at 37° C. Human dermal fibroblasts (Cascade Biologics, UK) were plated at a density of 25 cells/mm$^2$ in fibroblast growth medium (FM) (FM: Dulbecco's Modified Eagle's Medium, DMEM, containing 10% bovine calf serum) for 2 hours at 37° C. Cells were incubated with FM alone (control) or containing 10 nM selective β2-AR antagonist (ICI 118,551, Tocris) at time 0. The 35 mm glass-bottomed dishes were placed in a heating chamber, designed to maintain the medium between 35-37° C., and secured to the stage of an inverted Nikon Diaphot microscope as described in (Pullar (2006) *Chin Med J (Engl)* 116, 1029-33). "Speed" is the average speed in μm/min that the cells travel in a one-hour period of time, as shown in FIG. 1.

Floating and Anchored Collagen Gel Assays

A solution of bovine collagen types I (97 percent) and III (3 mg collagen/ml, Vitrogen 100, Collagen Corporation, Palo Alto, Calif.) was mixed with triple-strength DMEM, DMEM containing 20 mM Hepes buffer (Gibco, Grand Island, N.Y.) to maintain neutral pH, calf serum, cells (detached by trypsin from monolayer confluent cultures), and appropriate dilutions of a β2-adrenergic receptor agonist (ie salbutamol) and antagonist (ie ICI 118,551). The individual solutions were prepared and cooled to 4° C. before mixing to prevent premature gelation. The final solution contained 40% (v/v) Vitrogen, 20% DMEM, 30% DMEM with Hepes buffer, and 10% calf serum. Cells were incubated with the appropriate drug concentration for 30 minutes at 37° C. and added to the collagen gel mix just before gel casting at the concentration of 30,000 per ml. The lattices were cast, with 1.7 ml of the final solution per dish, in 35 mm bacteriologic dishes (Falcon Labware, BD Biosciences), to which fibroblasts poorly adhere. The mixture gelled within 30 minutes upon incubation at 37° C. in a humidified atmosphere of 95 percent air and 5 percent $CO_2$.

Figure 2:
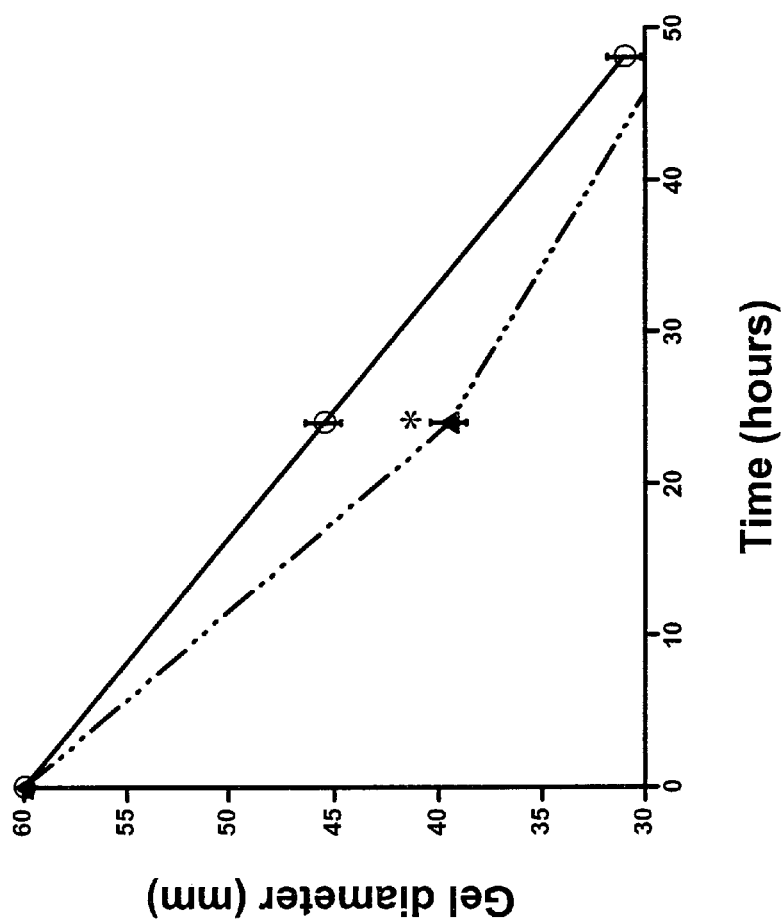
Figure 8:
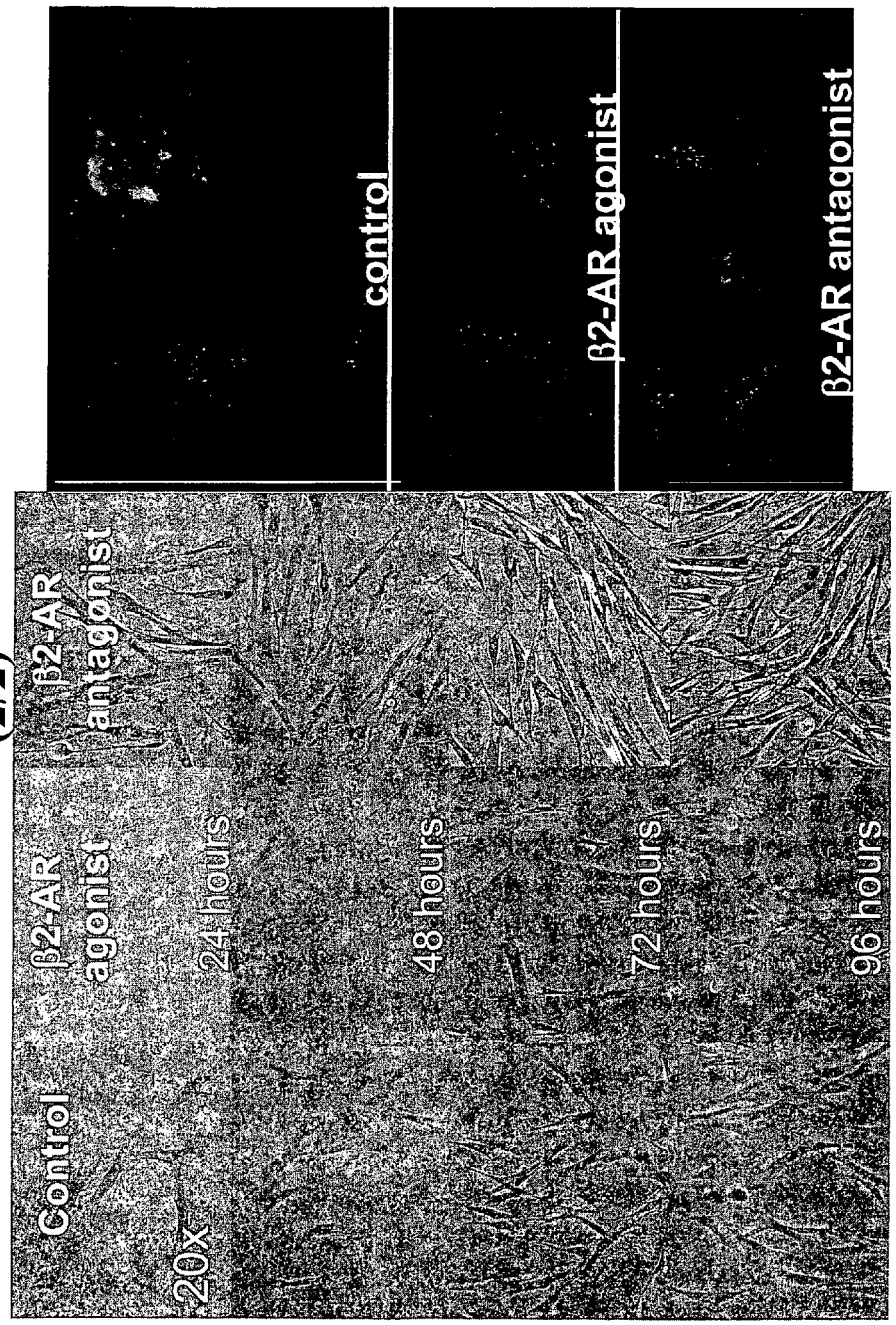
FIG. 8 shows that β2-AR agonists decrease fibroblast differentiation and function in a tethered collagen gel model, a 3D model of wounded dermis whereas, in contrast, β2-AR antagonists increase fibroblast differentiation and function in a tethered collagen gels.

To determine the effect of β2-AR antagonists on floating gel contraction (as shown in FIG. 2), lattices were detached from the sides of the dishes after 2 hours by rimming the edges of the dishes using a sterile 100 ml tip and gently shaking the dishes until the gels slid freely. Lattice retraction was measured every day by placing the dishes over a flat ruler on a black background. To determine the effect of β2-AR agonists and antagonists on proliferation of cells in a model of the wound dermis, the gels remained anchored to the side of the dish (as shown in FIG. 8).

Wound Model

FVB/NJ (β2-AR+/+) mice, were purchased from The Jackson laboratory (Bar Harbor, Me.). All animals used in the study were females between 8-12 weeks of age. β2-AR+/+ mice were anaesthetized by intraperitoneal injection of ketamine (100 mg/kg)/xylazine (10 mg/kg) (Pfizer). Back skin was shaved and two circular full-thickness 6 mm excisional wounds were created 2 cm apart, in the centre of the back, using a sterile 6 mm biopsy punch (SMS Inc.). Wounds were treated topically with 100 μl of hydroactive gel alone (Duoderm, ConvaTec) or containing 0.1% selective β2-AR agonist (salbutamol) or 0.1% selective β2-AR antagonist (ICI 118,551) immediately after wounding and daily thereafter until harvesting (n=5-7 mice per group, 2 wounds per mouse). Each mouse was housed separately after wounding until wound harvest. Wounds were left uncovered and digitally photographed, daily, to determine wound contraction over time. Wounds were harvested at days 3 and 5 post-wounding by carefully applying an 8 mm punch (SMS Inc.) around the original wound site and lightly pressing to form an outline on the skin. Scissors were then used to remove the wound site without damaging the delicate wound bed.

Tissue Harvesting, Immunohistochemistry and Analysis

For histological analysis the wounds were fixed in an IHC zinc fixative (BD Biosciences). The zinc-fixed biopsies were bisected to ensure that sections were taken from the centre of the wound, dehydrated through an ethanol xylene series, and embedded in paraffin. Cross-sections, 7 μM thick, were either stained using the hematoxylin-eosin technique (H & E) or stained with an antibody against smooth muscle α-actin (SMA, Dako) (FIGS. 4, 5 and 8B), collagen III (Rockland) (FIGS. 6 and 7), Ly6G-6C (a neutrophil marker, BD Pharmingen) (FIGS. 10 and 11), or F4-80 (a macrophage marker, Serotec) (FIGS. 12 and 13) followed by diaminobenzidine (DAB) detection (BD Pharmingen) according to Manufacturer's protocols.

Figure 3:
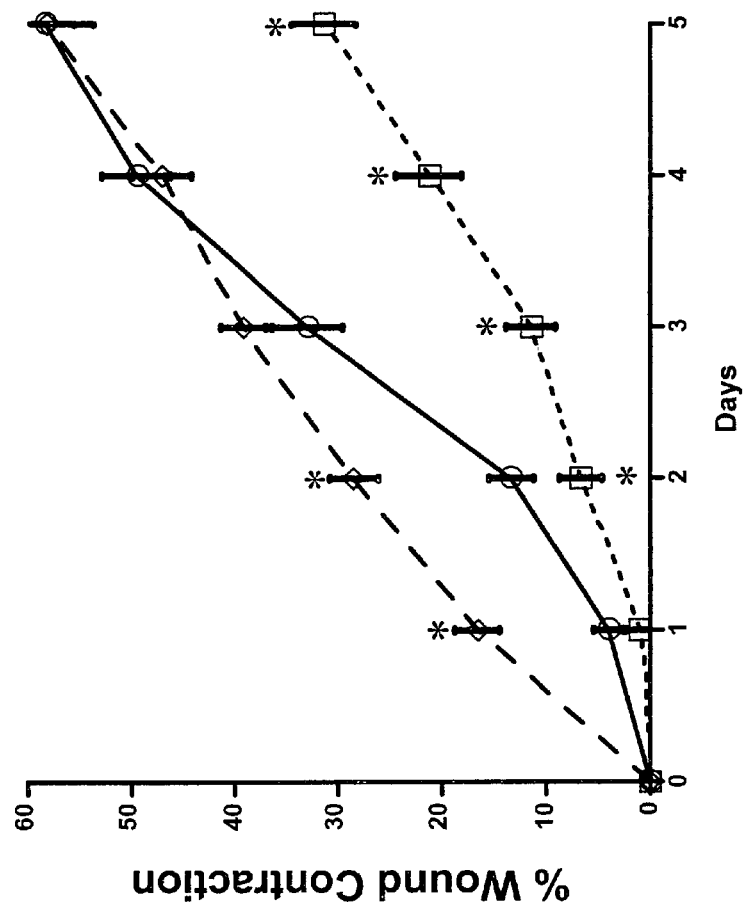
Figure 4:
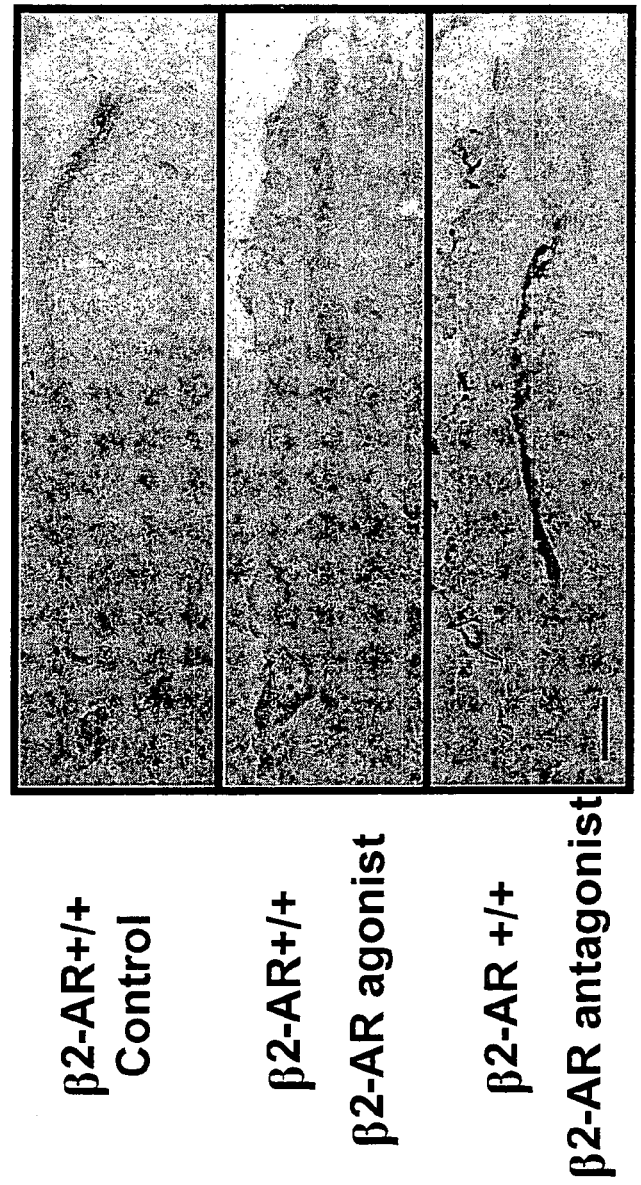
Figure 5:
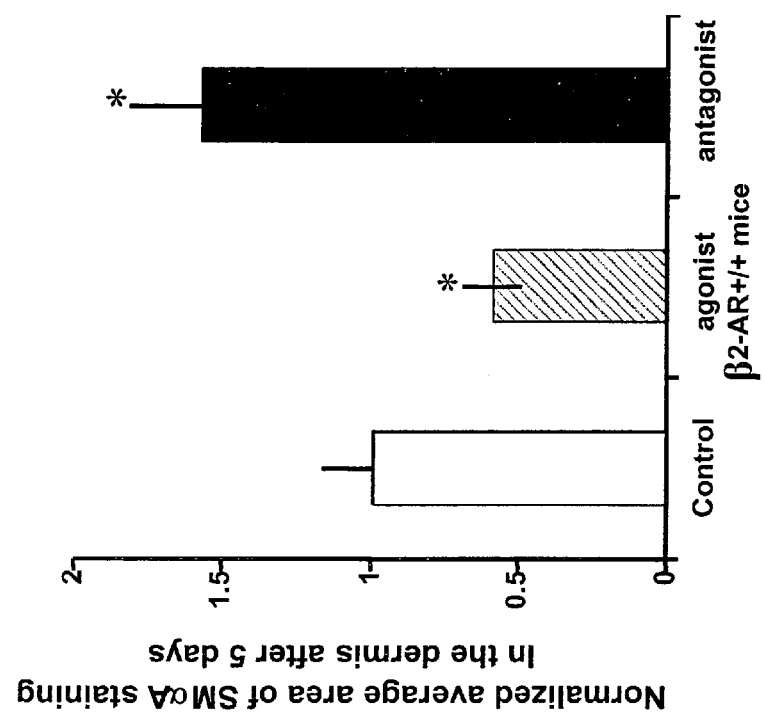
Figure 6:
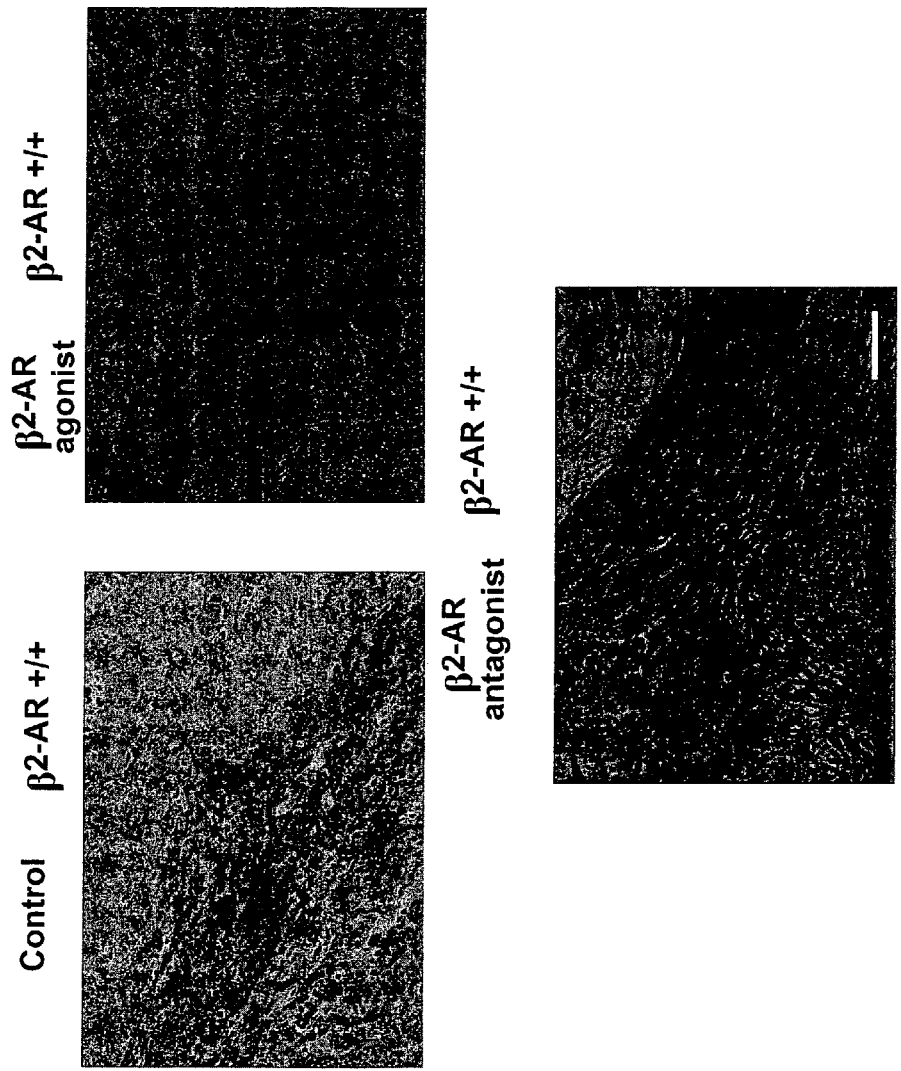
Figure 7:
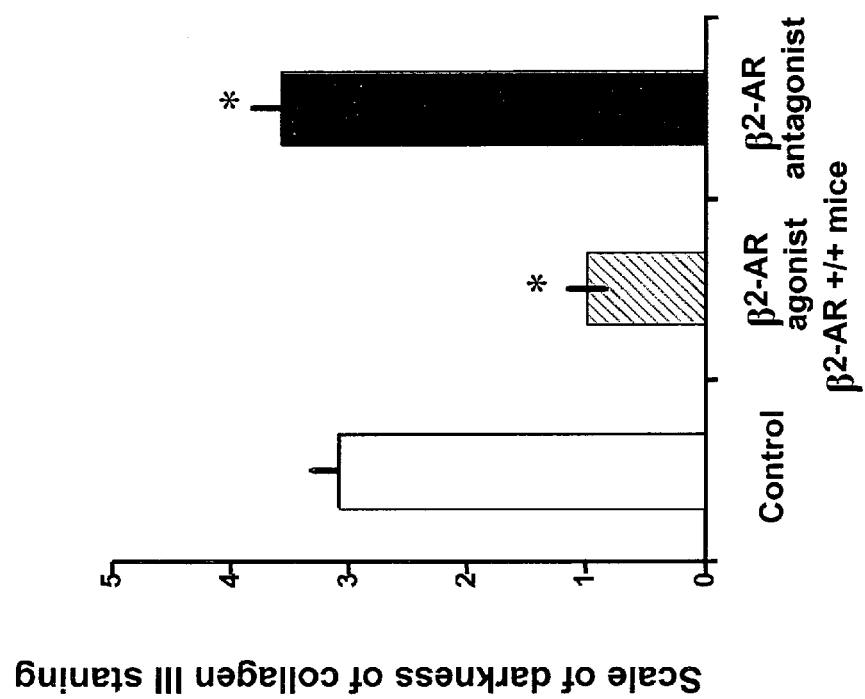
FIG. 7 is a bar chart showing that β2-AR antagonists increase the amount of collagen III staining in the wound dermis, 5 days post wounding, whereas β2-AR agonists decrease the amount of collagen III staining in the wound dermis, 5 days post wounding.

Specimens that were damaged in the histological process or otherwise non-interpretable were excluded from the study. Wound closure was quantified by measuring the wound area of each wound from the digital pictures taken every day with Image J, National Institutes of Health website. Each picture was calibrated individually (as shown in FIG. 3). Images of the smooth muscle-alpha actin (SMA)-stained wounds were captured at 2× magnification on a Nikon SMZ-U upright microscope with Nikon ACT-1 software (as shown in FIG. 4). Image J was used to determine the area of SMA staining in each wound to calculate the mean area of SMA staining in each group (as shown in FIG. 5). Images of the collagen III stained wounds were captured at 20× magnification on a Nikon Eclipse 2000U inverted microscope with NIS-Elements software (as shown in FIG. 6). The intensity of collagen III staining was graded on a scale of 0-6, no staining receiving a score of 0 and the darkest staining receiving a score of 6 (as shown in FIG. 7). The staining of each wound was scored in a double-blind manner and the mean staining intensity was calculated for each group.

Ten images of the Ly-6G-6C and F4-80-stained (6× magnification) wounds were captured on a Nikon Eclipse 2000U inverted microscope with MS-Elements software (FIGS. 10 and 12 show representative fields). The ten fields were selected from the dermis below the wound margins and across the wound bed using a template to ensure that images were captured from similar areas in each wound. The number of stained cells in each image was counted in a double-blind manner and the average cell number was calculated for each group (as shown in FIGS. 11 and 13).
Measurement of the Secretion of TGF-β1, TGF-β2, TGF-β3 and VEGF from Dermal Fibroblasts, and of VEGF from Neutrophils Human dermal fibroblasts (FIGS. 9 and 15) or human neutrophils (VEGF only) (FIG. 15) were seeded into 6-well plates and grown to 60% confluence in FM. The media was replaced at time 0 with media alone or containing 10 μM β2-AR agonist (salbutamol) or antagonist (ICI 118,551). The supernatants were prepared and assayed using ELISA kits for TGF-β1, TGF-β2, 15 TGF-β3 and VEGF (R & D systems) following the Manufacturer's instructions.
Method for Zebrafish Wounding Experiment The caudal fins of zebrafish embryos were transfected with a sterile scalpel blade 1 mm from the tip. Embryos were incubated at 28° C. for 6 hours in pond water +/−isoproterenol (non-specific β agonist), salbutamol (β2-specific agonist) or timolol (non-specific β2 antagonist) (all 10 μM), then incubated with fluorescein-tyramine (Perkin Elmer) followed by fixation. Embryose were imaged on a Nikon TE2000E inverted microscope system at 20× magnification (n=15-30).
Statistical Analysis Categorical variables were compared with a two-tailed Fisher Exact test while all continuous variables were compared with Student's t-test for unpaired data with unequal variance. The inventors considered P<0.05 to be significant.
Results Referring to FIG. 1, the inventor has demonstrated that β2-AR antagonists enhance dermal fibroblast migration. Furthermore, as shown in FIG. 2, β2-AR antagonists enhance the dermal-fibroblast-mediated contraction of floating collagen gels. Accordingly, in view of these observations, the inventor postulated that the β2-AR antagonist-mediated acceleration of wound repair may also decrease fibroblast action, and thereby reduce scarring.

In order to test this hypothesis, 6 mm punch wounds were created on the backs of female FVB mice. The full-thickness wounds were treated daily, topically, with 100 μl of a hydrogel alone or a hydrogel containing either 0.1% β2-AR agonist (salbutamol) or 0.1% β2-AR antagonist (ICI 118, 551). Referring to FIG. 3, there is shown the results of a macroscopic quantification of wound closure from daily digital photographs which confirmed the expected acceleration of wound closure upon application of the β2-AR antagonist, while wound closure was delayed in the β2-AR agonist-treated mice. Immunohistochemical staining of 5 μm sections from zinc-fixed, 5 paraffin-embedded wounds, 5 days post-wounding, demonstrated that, there was an increase in smooth muscle α-actin-expressing cells in β2-AR antagonist-treated wounds, compared to controls (as shown in FIGS. 4 and 5). In addition, FIGS. 6 and 7 demonstrate that there was an increase in collagen III deposition in β2-AR antagonist-treated wounds, compared to controls.

However, in contrast to β2-AR antagonist-treated wounds, as shown in FIGS. 4 and 5, β2-AR agonist-treated wounds contained less smooth muscle α-actin-expressing cells than untreated wounds. Furthermore, as shown in FIGS. 6 and 7, β2-AR agonist-treated wounds contained less collagen III deposition than untreated control wounds. Therefore, in view of these data, it appeared that β2-AR antagonist treatment enhances wound closure, possibly reducing scarring.

In order to model the wound dermis in vitro, dermal fibroblasts were seeded into adherent collagen gels, which mimic the mechanical stress present in the wound bed (Grinnell, 2003, *Trends Cell Biol* 13, 264-9). Fibroblasts in anchored matrices will proliferate and adopt the elongated, bipolar morphology characteristic of myofibroblasts (Arora et al (1999) *Am J Pathol* 154, 871-82), while fibroblasts seeded into floating matrices will become quiescent within a few days. 50% collagen I gels were seeded with 30,000 cells per ml in the absence or presence of a β2-AR agonist or a β2-AR antagonist. As shown in FIG. 8, while β2-AR antagonist treated gels contained rapidly proliferating fibroblasts and remained anchored, untreated gels began to retract within 96 hours. However, β2-AR agonist-treatment decreased the proliferation of fibroblasts in the gels, resulting in loss of tension and release of the gel from the plate within 72 hours.

TGF-β1 is known to stimulate the proliferation of dermal fibroblasts (Ghahary et al (2002) *Wound Repair Regen* 10, 328-35). Hence, the inventor hypothesised that β2-AR antagonists may increase the production of TGF-β1 and/or TGF-β2 and perhaps reduce TGF-β3 in the anchored gels generating prolonged fibroblast proliferation, and set out to test this hypothesis. Dermal fibroblasts were therefore grown in the absence or presence of either a β2-AR antagonist (ICI 118,551) or a β2-AR agonist (salbutamol) for 24 hours. The supernatants were collected, and ELISAs were performed to determine the amounts of TGF-β1, TGF-62 and TGF-β3 secreted by the dermal fibroblasts. As shown in FIG. 9, β2-AR antagonist treatment increased TGF-β1 levels 3-fold and TGF-β2 levels 1.6-fold, while having no effect on the levels of TGF-β3. However, surprisingly, β2-AR agonists significantly decreased the amount of TGF-β1 that was secreted from fibroblasts by 4-fold and increased the amount of TGF-β3 secreted by 5-fold. The inventor was therefore most surprised to observe that the β2-AR agonist-mediated alterations in TGF-β1 and TGF-β3 levels reflect the relative levels of cytokines found in embryonic wounds, which do not scar (Redd et al (2004) *Philos Trans R Soc Lond B Biol Sci* 359, 777-84.). Indeed, reducing TGF-β1 levels at the adult wound site is known to reduce scar formation, while adding recombinant TGF-β3 to adult wounds is known to reduce inflammation, matrix deposition, and thus scarring (Shah et al (1995) *J Cell Sci* 108 (Pt 3), 985-1002).

In adult wounds, degranulating platelets from damaged blood vessels release a cocktail of cytokines and growth factors. The growth factor cocktail promotes a rapid inflammatory response, initiating inflammatory cell chemotaxis to the wound. Neutrophils migrate into the wound site within hours of wounding, while macrophages are recruited to wounds after 2-3 days where they become a major source of growth factors, including the pro-fibrotic growth factor, TGF-β1. In contrast, embryos lack platelets and the inflammatory cell lineages develop fairly late in embryonic development. Accordingly, the cytokine/growth factor profile of an embryonic wound is markedly different from that of an adult wound. Embryonic wounds have decreased levels of TGF-β1 and β2 and increased levels of TGF-β3 and no inflammatory response. Neutralising TGF-β1 and β2 or enhancing levels of TGF-β3 can produce scarless healing in adult mice, rats and pigs.

Although the inventor does not wish to be bound by any hypothesis, she believes that reducing the recruitment of inflammatory cells to the wound could decrease the levels of TGF-β1 in the wound, and thereby reduce fibrosis and scarring. She therefore set out to test this hypothesis upon addition of a selective β2-AR agonist to wounds.

Referring to FIGS. 10 and 11, the addition of β2-AR agonist to wounds in vivo decreased the numbers of neutrophils present in the wound 3 days after wounding. Furthermore, referring to FIGS. 12 and 13, the addition of β2-AR agonist to wounds in vivo decreased the numbers of macrophages present in the wound, 3 days post wounding. The inventor, postulates that a β2-AR agonist-mediated decrease in inflammation could also contribute to its antiscarring, anti-fibrotic effects.

CONCLUSIONS

The inventor has demonstrated that application of a selective β2-AR agonist, such as salbutamol, to a wound site, results in a decrease in the amount of TGF-β1 and a concomitant increase in the amount of TGF-β3 and that this mediates an alteration in fibroblast function, activity and differentiation. These changes in fibroblast function, activity and differentiation result in a reduction in the deposition of collagen and decrease in the accumulation of aberrantly remodelled collagen. Hence, the inventor believes that a selective β2-AR agonist could be used as an effective treatment for a number of medical conditions characterised by aberrant fibrosis where induced by trauma or as a result of iatragenesis or metabolic or genetic susceptibility.

Similarly, a β2-AR antagonist is considered to be effective under conditions where an increase in fibroblast differentiation and concomitant increase in collagen deposition is required, such as where a reduction in wrinkles of the skin is required.

The invention claimed is:

1. A method for combating formation of a keloid scar or a hypertrophic scar, the method comprising: administering to a subject who has at least one scar selected from the group consisting of a keloid scar and a hypertrophic scar, an agent which positively modulates β2-adrenergic receptor, wherein the agent is selected from salbutamol, fenoterol, butoxamine, clenbuterol, formoterol or salmeterol.

2. The method according to claim 1, wherein the agent is administered orally to the subject.

3. The method according to claim 2, wherein the agent is administered by inhalation.

4. The method according to claim 1, wherein the agent is provided on a vehicle to cover a wound site of the subject.

5. The method according to claim 4, wherein the vehicle is a sterile dressing or patch.

6. The method according to claim 1, wherein the agent is incorporated within a slow or delayed release device.

7. The method according to claim 6, wherein the slow or delayed release device is administered by insertion on or under skin of the subject.

8. The method according to claim 1, wherein the agent is administered to the subject by injection.

9. The method according to claim 8, wherein the injection is into a wound.

10. The method according to claim 1, wherein the agent is administered in an amount of 0.001 ng to 100 mg per 24 hours.

11. A method for combating formation of a keloid scar or a hypertrophic scar the method administering to a subject who has at least one scar selected from the group consisting of a keloid scar and a hypertrophic scar, an agent which positively modulates P2-adrenergic receptor, wherein the agent is selected from salbutamol, fenoterol, butoxamine, clenbuterol, formoterol or salmeterol, in combination with one or more of: corticosteroid injections, cryotherapy, topical silicone sheets, radiation, pressure garments, and Imiquimod.

12. The method according to claim 11, wherein the agent is administered orally, topically, on a vehicle for covering a wound site, within a slow or delayed release device, or by injection.

* * * * *